(12) United States Patent
Alexander et al.

(10) Patent No.: US 11,097,236 B2
(45) Date of Patent: Aug. 24, 2021

(54) MAGNETIC MIXERS

(71) Applicant: Global Life Sciences Solutions USA LLC, Marlborough, MA (US)

(72) Inventors: James Pellegrino Alexander, Niskayuna, NY (US); Klaus Gebauer, Uppsala (SE); David Allan Torrey, Niskayuna, NY (US); Ashraf Said Atalla, Niskayuna, NY (US); Sima Didari, Niskayuna, NY (US); Richard Lee Damren, Marlborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 0 days.

(21) Appl. No.: 16/089,163

(22) PCT Filed: Mar. 8, 2017

(86) PCT No.: PCT/US2017/021412
§ 371 (c)(1),
(2) Date: Sep. 27, 2018

(87) PCT Pub. No.: WO2017/172316
PCT Pub. Date: Oct. 5, 2017

(65) Prior Publication Data
US 2019/0282980 A1    Sep. 19, 2019

Related U.S. Application Data

(63) Continuation-in-part of application No. 15/087,656, filed on Mar. 31, 2016, now Pat. No. 10,335,750,
(Continued)

(51) Int. Cl.
*B01F 13/08* (2006.01)
*H02K 5/128* (2006.01)
(Continued)

(52) U.S. Cl.
CPC .......... *B01F 13/0827* (2013.01); *B01F 13/08* (2013.01); *C12M 27/02* (2013.01);
(Continued)

(58) Field of Classification Search
CPC .................................................. B01F 13/0827
(Continued)

(56) References Cited

U.S. PATENT DOCUMENTS 2,566,743 A    9/1951   Okulitch et al.
2,990,256 A *  6/1961   Lovins ...................... C30B 7/00
                                                    117/202
(Continued)

FOREIGN PATENT DOCUMENTS

CN         204068642 U    12/2014
CN         105327639 A     2/2016
(Continued)

OTHER PUBLICATIONS

International Search Report dated Sep. 11, 2017 from corresponding PCT Patent Application No. PCT/US2017/021412.
(Continued)

*Primary Examiner* — David L Sorkin
(74) *Attorney, Agent, or Firm* — Jeff Vockrodt; Culhane Meadows, PLLC

(57) ABSTRACT

The system and method of the invention pertains to an axial flux stator is implemented to replace the drive-end magnets and the drive motor. The axial flux stator comprises a control circuit to control the voltage and current provided to the stator, to measure the torque and speed of rotation, and to measure the magnetic flux and magnetic flux density produced by the axial flux stator and impeller magnets, individually or in combination. The axial flux stator comprises a plurality of current carrying elements to produce magnetic flux in an axial direction and drive the impeller.

15 Claims, 30 Drawing Sheets

Related U.S. Application Data which is a continuation-in-part of application No. 15/087,712, filed on Mar. 31, 2016, now Pat. No. 10,583,409, which is a continuation-in-part of application No. 15/166,397, filed on May 27, 2016, now Pat. No. 10,682,618.

(51) Int. Cl.
| | |
|---|---|
| *H02K 21/24* | (2006.01) |
| *C12M 1/06* | (2006.01) |
| *H02K 1/14* | (2006.01) |
| *H02K 49/10* | (2006.01) |

(52) U.S. Cl.
CPC ............ *H02K 1/146* (2013.01); *H02K 5/128* (2013.01); *H02K 5/1282* (2013.01); *H02K 21/24* (2013.01); *H02K 49/108* (2013.01)

(58) Field of Classification Search
USPC .................................................. 366/273, 274
See application file for complete search history.

(56) References Cited

U.S. PATENT DOCUMENTS

| | | | |
|---|---|---|---|
| 3,764,836 | A | 10/1973 | Bender et al. |
| 4,209,259 | A | 6/1980 | Rains et al. |
| 4,498,785 | A | 2/1985 | De Bruyne |
| 4,594,883 | A | 6/1986 | Pollard |
| 5,259,670 | A | 11/1993 | Brown |
| 5,332,374 | A | 7/1994 | Kricker et al. |
| 5,470,152 | A | 11/1995 | Rains |
| 5,478,149 | A | 12/1995 | Quigg |
| 6,336,603 | B1 | 1/2002 | Karkos, Jr. et al. |
| 6,607,370 | B2 | 8/2003 | Fukamachi et al. |
| 7,434,983 | B2 | 10/2008 | Terentiev |
| 7,743,674 | B2 | 6/2010 | Boncan et al. |
| 8,009,001 | B1 | 8/2011 | Cleveland |
| 8,024,962 | B2 | 9/2011 | Tonmukayakul et al. |
| 8,182,137 | B2 | 5/2012 | Terentiev |
| 8,845,181 | B2 | 9/2014 | Castillo et al. |
| 8,885,035 | B2 | 11/2014 | Ludwig |
| 8,894,756 | B2 | 11/2014 | Galliher et al. |
| 2002/0041537 | A1 | 4/2002 | Yale |
| 2002/0082173 | A1* | 6/2002 | Terentiev .............. A61M 1/127 505/163 |
| 2002/0145940 | A1* | 10/2002 | Terentiev ............ B01F 13/0818 366/273 |
| 2004/0047232 | A1* | 3/2004 | Terentiev ............ B01F 7/00908 366/273 |
| 2005/0002274 | A1 | 1/2005 | Terentiev |
| 2005/0258821 | A1 | 11/2005 | Wang et al. |
| 2006/0092761 | A1 | 5/2006 | Terentiev |
| 2009/0104594 | A1 | 4/2009 | Webb |
| 2010/0214867 | A1 | 8/2010 | Karkos, Jr. et al. |
| 2011/0025161 | A1 | 2/2011 | Ashe et al. |
| 2011/0176943 | A1 | 7/2011 | Tran et al. |
| 2012/0149091 | A1 | 6/2012 | Wilkerson et al. |
| 2012/0228978 | A1 | 9/2012 | Petro et al. |
| 2013/0301375 | A1 | 11/2013 | Stephan et al. |
| 2014/0157876 | A1 | 6/2014 | Anderson et al. |
| 2015/0259638 | A1 | 9/2015 | Zeuch et al. |
| 2015/0367302 | A1 | 12/2015 | Gebauer |
| 2016/0047184 | A1 | 2/2016 | Lucharucka et al. |
| 2017/0216798 | A1 | 8/2017 | Boettcher et al. |
| 2017/0282137 | A1 | 10/2017 | Atalla et al. |
| 2017/0341043 | A1 | 11/2017 | Atalla et al. |

FOREIGN PATENT DOCUMENTS

| | | |
|---|---|---|
| EP | 1188474 A1 | 3/2002 |
| EP | 2813281 A1 | 12/2014 |
| JP | 61212275 A | 9/1986 |
| JP | U60135041 | 12/1986 |
| JP | 2007522801 A | 8/2007 |
| JP | 2008086115 A | 4/2008 |
| WO | 2005068059 A1 | 7/2005 |
| WO | 2009132874 A2 | 11/2009 |
| WO | 2010082817 A2 | 7/2010 |

OTHER PUBLICATIONS

U.S. Office Action corresponding to U.S. Appl. No. 15/166,397, dated Feb. 25, 2019.

International Invitation to Pay Additional Fees issued in connection with corresponding PCT Application No. PCT/US2017/021412, dated Jul. 18, 2017.

International Search Report and Written Opinion issued in connection with corresponding PCT Application No. PCT/US2017/021412, dated Sep. 11, 2017.

Rezazadeh et al., "Simultaneous measurement of fluids viscosity and denisty using a microbeam", Perspective Technologies and Methods in MEMS Design, 2009. MEMSTECH 2009. 2009 5th International Conference on, pp. 36-44, Apr. 22-24, 2009, Zakarpattya.

Jakoby et al., "Miniaturized sensors for the viscosity and density of liquids—performance and issues", IEEE Transactions on Ultrasonics, Ferroelectrics, and Frequency Control, vol. 57, Issue 1, pp. 111-120, Jan. 2010.

Office Action received in Japanese Application No. 2018-550547 dated Apr. 19, 2021, with partial translation, 8 pages.

* cited by examiner

MAGNETIC MIXERS

CROSS-REFERENCE TO RELATED APPLICATIONS

This application claims the benefit of PCT International Application No. PCT/US2017/021412, having the International Filing Date of Mar. 8, 2017, and is a continuation-in-part of U.S. patent application Ser. No. 15/087,712, filed on Mar. 31, 2016, a continuation-in-part of U.S. patent application Ser. No. 15/087,656, filed on Mar. 31, 2016, and a continuation-in-part of U.S. patent application Ser. No. 15/166,397, filed on May 27, 2016, the entire disclosures of each of which are hereby incorporated by reference.

FIELD

Embodiments relate generally to the field of bioreactors, and more particularly to a magnetic mixer drive for a bioreactor.

BACKGROUND

Mixers and pumps have a wide range of applications including bioreactors. The main elements in a rotary mixer 100 (FIG. 1A) are the drive 14 (which contains the driving mechanism) and the impeller 12 (which contains the mixing blades), at the impeller end 11. The two elements are aligned and coupled together by different topologies. In one aspect, the magnetic coupling is where the impeller 12 holds a set of magnets 10 that are coupled to the drive end 13. This is established by a set of magnets in the drive end rotated by a separate motor. The existing technology contains a set of cylindrical magnets 14 (See FIG. 1B) on each end separated by a certain "magnetic" gap 16 which is primarily composed of air, fixing elements, and mixing bag wall which are all non-magnetic elements. The existing technology suffers many impediments, including, but not limited to: (1) the weak coupling between the magnets which requires using more expensive and larger magnets (e.g., Neodymium magnets), (2) poor volume utilization, (3) the use of rare-earth magnets in the impeller which is a single use element that increases the cost of the impeller and poses environmental challenges, and (4) large drive size, as it constructs of a set of large coupling magnets driven by a separate electrical motor.

Mixing systems often include an agitator or impeller mechanically connected to a drive shaft lowered into a fluid through an opening in the top of a vessel. The drive shaft is connected to an electric motor arranged outside the vessel. In a closed vessel, a fluid seal is provided between the drive shaft and the wall of the vessel to prevent leakage of fluid from the vessel. Other mixing systems include a rotating magnetic drive head outside of the vessel and a rotating magnetic impeller as an agitation element within the vessel. The movement of the magnetic drive head enables torque transfer and thus rotation of the magnetic impeller allowing the impeller to mix and agitate the fluid within the vessel. Because there is no need in a closed vessel to have a drive shaft penetrate the vessel wall to mechanically rotate the impeller, magnetically coupled systems can eliminate the need for having fluid seals between the drive shaft and the vessel. Magnetic coupling of an impeller inside the vessel to a drive system or motor external to the vessel can eliminate contamination issues, allow for a completely enclosed system, and prevent leakage.

Increasingly, in the biopharmaceutical industry, single use or disposable containers or vessels are used as close type systems, typically in range of about 1-2000 liters. The vessel may be a tank-type support with for example substantially cylindrical shape and is made of rigid material such as stainless steel to provide sufficient support for the flexible bag or container, for example of a kind used in single-use bioreactors. Use of sterilized disposable bags eliminates time consuming steps of cleaning of the vessel and reduces the chance of contamination. The flexible container or bag is placed inside the vessel in an accurate manner so that for example different pipelines or tubes, mixers and sensors can be connected to the bag properly and accurately.

Combining the single use or disposable bags with a magnetic agitator system establishes a sterile environment that is utilized in biopharmaceutical manufacturing. A variety of vessels, devices, components and unit operations for mixing and manipulating liquids and/or for carrying out biochemical and/or biological processes are available. For example, biological materials including mammalian, plant or insect cells and microbial cultures can be processed using bioreactors that include single-use processing bags. Manufacturing of complex biological products such as proteins, monoclonal antibodies, etc. requires, in many instances, multiple processing steps ranging from fermentation or cell culture (bacteria, yeast, insect, fungi, etc.), to primary recovery and purification.

It is desirable to address the needs as stated above by utilizing less expensive elements that are more environmentally friendly. Aspects of the invention will run a much smaller impeller, and have a reduced magnetic force that will allow the bag to be separated from the drive more easily. Further, moving parts on the drive (user) end will be addressed to provide safer mechanisms.

The movement of the magnetic drive head enables torque transfer and thus rotation of the magnetic impeller allowing the impeller inside the vessel to mix and agitate the fluid within the vessel without providing a sealed shaft. The magnetic mixing principle is especially advantageous when using completely closed vessels, or when utilizing containers as required to maintain sterility of the internal volume and the fluid to be mixed.

In single-use processing technology, as employed in the production of biopharmaceuticals, plastic containers and bags are used which are typically pre-sterilized (e.g., by gamma irradiation), and employed as completely closed systems connected to adjacent fluid processing equipment and lines using aseptic connections. In these applications of single-use mixing vessels and bioreactors, the use of magnetic mixing technology is preferred for reasons of process safety, simplicity and the lower cost that comes by omitting complex sealing arrangements around rotating shafts.

Today, certain challenges are imposed on processes employing magnetic mixing technology where a direct and permanent mechanical connection between impeller and external drive by a shaft is lacking. These deficiencies include not knowing the actual speed of the impeller; and the torque and power input are more difficult to assess compared with a direct mechanical coupling. Further, as the power transferred by magnetic couplings is generally limited compared to mechanical shafts, magnetic mixers are typically operating at lower power input which makes it difficult to assess power input and torque on the background of frictional forces, disturbances and noise in such measurements. Therefore, there is a need to improve the assessment, measurement and control of magnetic mixing and magnetic mixer couplings.

In more details, challenges with current magnetic mixers include: (1) indirect (not real-time) determination of power delivered to the fluid, as performed with user-interface manipulation of formulas or look-up tables; (2) fluid density and/or viscosity changes as the mixing process takes place, without accurate control of the mixing process; and (3) inability to identify abnormalities in the mixing process. No feature or direct process in bioreactors used to date can detect or flag such issues.

Moreover, no existing solution provides for a direct measure of the power delivered to the fluid while mixing. Prior methods have been dependent on look-up tables to calculate the power delivered to fluid. In addition, no device or method has been able to continuously monitor the fluid viscosity and density or to detect abnormalities in mixing process without the look-up tables as suggested prior.

It is desirable to address the needs as stated above by providing additional functionality to a bioreactor and/or mixer. It will allow accurate monitoring of the power delivered to the fluid while mixing, and will provide more accurate control by a user. It will also beneficially permit continuous updates of the fluid properties, and preferentially, alarms in cases of abnormalities in mixing, such as, for example, in the circumstance of 'flooding' of impellers when the ratio of volumetric gas to liquid ratio exceeds a threshold.

SUMMARY

The system and method of the invention pertains to a magnetic drive for a bioreactor mixer or pump that strengthens the magnetic coupling to provide higher torque and replace the drive-end magnets and drive motor. Embodiments disclosed herein use a back iron on both ends to strengthen the magnetic coupling as well as pie-shaped magnets ("pie" shaped in the sense of a wedge shape and format (i.e., triangular/trapezoidal have a wider outer edge and smaller inner dimension, or shaped as a circular or annular sector) to increase the volume utilization and hence provide higher torque and allow the use of less expensive material (e.g. ferrites). In another embodiment, the rotor side is constructed with a Halbach array which increases the torque without the need to add a back iron piece. Another embodiment implements an axial flux stator to replace the drive-end magnets and the drive motor.

In one embodiment, a system is described to be utilized as bioreactor mixer, the system comprising: a rotation drive, an impeller capable of rotating around a central (rotational) axis, and a plurality of magnets positioned in one or more array formats, a first set of magnets in a first array format positioned at a drive end adjacent the rotation drive and a second set of magnets in a second array format positioned at the impeller; wherein the rotation drive is a drive stator.

In one aspect, the system has a drive stator that is an axial flux stator. In another aspect, the axial flux stator is positioned on an underside of the plurality of magnets. The axial flux stator comprises a control circuit to control the voltage and current, individually or in combination, provided to the stator. The axial flux stator comprises a control circuit to measure the torque and speed of rotation. The axial flux stator comprises a control circuit to measure the magnetic flux and magnetic flux density produced by the axial flux stator and impeller magnets. The axial flux stator comprises a plurality of current carrying elements to produce magnetic flux in an axial direction and drive the impeller.

The axial flux stator in embodiments described herein comprises a core to fix the current carrying elements upon, or affix the current carrying elements thereto. Aspects of the embodiments disclosed thus permit the core to be magnetic or non-magnetic.

Another embodiment is a mixing system comprising: a stator comprising a plurality of current carrying elements to produce a magnetic flux in an axial direction, an impeller capable of rotating around an axis of the axial flux stator; wherein the magnetic flux drives the impeller. The stator is an axial flux stator having a core to affix the current carrying elements, the core including stator teeth. The core is magnetic in one aspect, and may also be non-magnetic.

Various embodiments include an impeller comprising a plurality of magnets, a back plate to enhance the magnetic coupling, a plurality of current carrying elements, one or more mixing blades, and/or a fixture to support the impeller from misalignment, alone or in combination.

One embodiment of a system is utilized as bioreactor mixer, the system comprising: a rotation drive, an impeller capable of rotating around a central (rotational) axis, a plurality of magnets positioned in one or more array formats, a first set of magnets in a first array format positioned at a drive end adjacent the rotation drive and a second set of magnets in a second array format positioned at the impeller, and at least one plate including the first set of magnets positioned thereon such that the first set of magnets are positioned in a concentric geometric configuration and individually shaped with a wider outside dimension that narrows toward a center of the concentric geometric configuration; wherein the second set of magnets are arranged adjacent one another to augment a magnetic field on one side of the second array while cancelling the magnetic field to zero on an opposite side of the second array to achieve a spatially rotating pattern of magnetization. In one aspect, the system further comprises an external vessel into which at least a portion of the bioreactor mixer is placed.

In another embodiment, a system is utilized as bioreactor mixer, the system comprising: a rotation drive, an impeller capable of rotating around a central (rotational) axis, a plurality of magnets positioned in one or more array formats, a first set of magnets in a first array format positioned at a drive end adjacent the rotation drive and a second set of magnets in a second array format positioned at the impeller, and at least a first plate including the first set of magnets positioned thereon; wherein the second set of magnets are positioned with a second plate comprising a material having magnetic permeability greater than the magnetic permeability of air and sandwiched between the first set of magnets and the impeller, such that a magnetic field gradient is created between the first array format of the first set of magnets and the second array format of the second set of magnets.

In one aspect, the first plate comprises a material having magnetic permeability greater than the magnetic permeability of air. The first set of magnets can be positioned in an array format geometrically shaped with a wider outside dimension that narrows toward a concentric center. The second set of magnets can be positioned in an array format geometrically shaped with a wider outside dimension that narrows toward a concentric center.

Embodiments of the invention disclose a system and method that utilize a torque sensor, and the measured torque associated with the sensor, to detect the different fluid and mixing properties, conditions, and abnormalities in a mixing process. The torque produced in the mixing process relates to different fluid properties such as viscosity and density. It also relates to different mixing conditions such as presence of obstacles and changes or issue with gas sparging. Moreover, torque measurements enable determination of power transmitted to a fluid by actual measurement, in contrast to using solely empirical impeller power number and speed, and allow actual mass transfer determination (i.e., gas transfer calculations).

Embodiments disclosed regard a torque sensor (e.g., transducer) and a method of using the measured torque to detect the different fluid and mixing properties, conditions, and abnormalities.

In one embodiment, a magnetic mixing system characterizes conditions in a fluid mixing device, the system comprising: a vessel comprising a fluid; a drive that creates a magnetic field; a controller that operates the drive; one or more sensors positioned with the system to detect the magnetic field or a magnetic flux; and a processor receiving information from the sensors to calculate one or more of power provided to the fluid, torque and speed of the impeller. The magnetic mixing system further comprises an impeller inside the vessel, wherein the drive creates the magnetic field to rotate the impeller and the sensors measure the magnetic field or the magnetic flux provided to the impeller. The one or more sensors are positioned with the drive, the impeller, or between the impeller and the drive. The sensors can further detect current and voltage provided to the drive.

In one aspect, the drive as a stator, or the drive can include a set of permanent magnets in combination with a motor. In another aspect, the drive is a stator, motor, or magnetic coupling, and the sensors are transducers positioned therewith, respectively, alone or in combination.

Embodiments of the application, utilize the torque and speed of the impeller as it corresponds to torque and speed in mixing of the fluid. The processor uses the power, torque or speed, alone or in combination, with one or more fluidic properties to assess real-time mixing conditions and mixing properties. In addition, the processor detects a change in the fluidic properties, mixing conditions, or mixing properties, individually or in combination. In another embodiment, the processor detects abnormalities in the fluidic properties, mixing conditions, or mixing properties as determined by learned patterns or predetermined threshold values. The fluidic properties include any number of characteristic compositions, including density and viscosity of the fluid, among others. The processor detects abnormalities in the density or viscosity of the fluid, in the power, torque, or speed, alone or in combination. Further, the processor can detect blockage, gas dispersion, or one or more contaminants in the fluid, alone or in combination.

Embodiments disclosed herein provide a processor that is an analyzer to provide direction to the controller in a feedback loop. The analyzer directs power to the drive to increase or decrease agitation, to adjust fluidic properties, and correct any deficiencies or abnormalities, individually or in combination.

Thus described, one embodiment discloses a method of controlling conditions in a fluid mixing device, the method comprising the steps of: providing the fluid mixing device having a vessel comprising a fluid, a drive that creates a magnetic field, a controller that operates the drive, one or more sensors, and a processor; detecting, by way of the one or more sensors, at least one of a magnetic field, a magnetic flux, power provided to the fluid, torque, speed, current, or voltage; calculating power, torque and speed of the impeller, if not previously detected; and analyzing, by way of the processor, using the power, torque and speed to determine one or more fluidic properties of the fluid, real-time mixing conditions and mixing properties. In one aspect, the mixing system further comprises an impeller and the step of detecting includes detecting a position of the impeller. The step of analyzing includes detecting a change in the fluidic properties.

In addition, the power, torque, speed, current, voltage, fluidic properties, mixing conditions, and mixing properties, alone or in combination, are displayed at a user-interface. The power, torque and speed are determined directly, without user manipulation.

Aspects of the disclosed embodiments include fluidic properties comprising fluid composition, density, and viscosity, alone or in combination, provided to the processor by way of the sensors. The method further comprises a step of identifying abnormalities in the fluid mixing device, the fluidic properties, the mixing conditions, and the mixing properties. The processor can be an analyzer that provides feedback to the controller to automatically control the power, torque, and speed delivered to the drive. In one aspect, the processor provides a pre-determined composition, viscosity and density of the fluid, alone or in combination. In another aspect, the processor provides information to the controller that determines an optimal composition, viscosity, and density as based on a change in the fluidic properties.

Further aspects allow the sensors to detect any number of attributes, characteristics, or otherwise, including, without limitation, detecting an angle between the drive and the impeller during operation of the fluid mixing device in order to determine the fluidic properties.

Embodiments thus provide additional functionality to a user of the bioreactor or mixer. Accurate monitoring of power delivered to the fluid while mixing is now possible, in real-time, allows continuous updates and adjustments as to the fluid properties. In another aspect, alarms are implemented, as desired, in cases of abnormalities in the mixing process.

Detailed descriptions of various embodiments are described as follows.

DETAILED DESCRIPTION

Figure 1A:
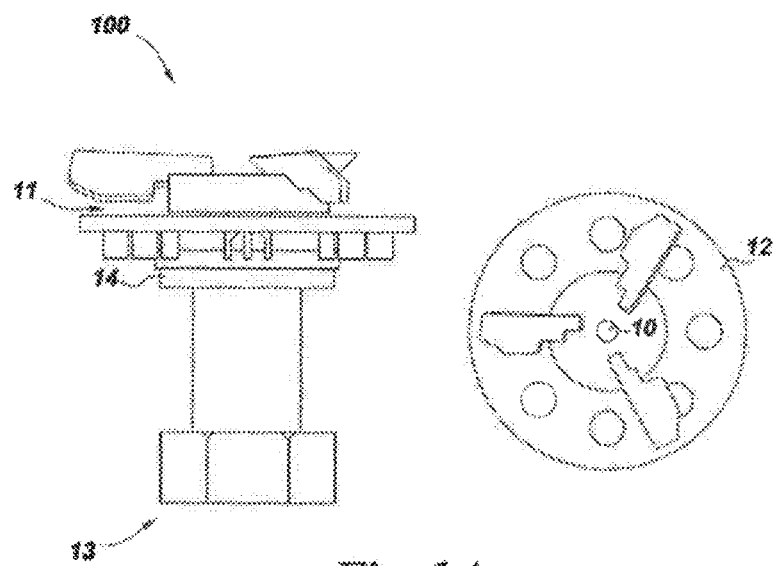
FIG. 1A (PRIOR ART) illustrates the magnetic drive for a bioreactor mixer.
Figure 1B:
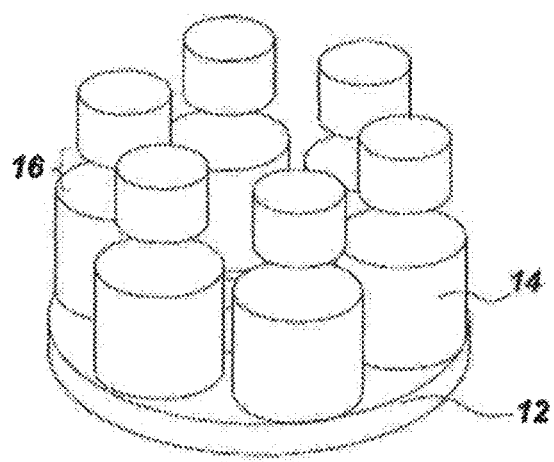
FIG. 1B (PRIOR ART) illustrates a magnetic coupling where the impeller holds a set of magnets that are coupled to the drive end, the set of magnets in the drive end rotated by a separate motor.

Various embodiments will be better understood when read in conjunction with the appended drawings. It should be understood that the various embodiments are not limited to the arrangements and instrumentality shown in the drawings.

The system and method of the embodiments disclosed pertain to a magnetic drive for a bioreactor mixer or pump that strengthens the magnetic coupling to provide higher torque and replace the drive-end magnets and/or drive motor, as desired. Embodiments include magnetic shapes and arrangements as well, including pie-shaped magnets ("pie" shaped in the sense of a wedge shape and wedged format (i.e., triangular/trapezoidal have a wider outer edge and smaller inner dimension, or shaped as a circular or annular sector), such that the wedges fit together to increase the volume utilization and hence provide higher torque, and further allow the use of less expensive material (e.g. ferrites). In one embodiment, the rotor side is constructed with a Halbach array which increases the torque. Embodiments disclosed may utilize a back iron on one or both ends to strengthen the magnetic coupling. With the Halbach array, torque is increased without a back iron piece. Another embodiment implements an axial flux stator to replace the drive-end magnets and the drive motor. Embodiments are disclosed as follows.

Disposable Bioreactors

Figure 27:
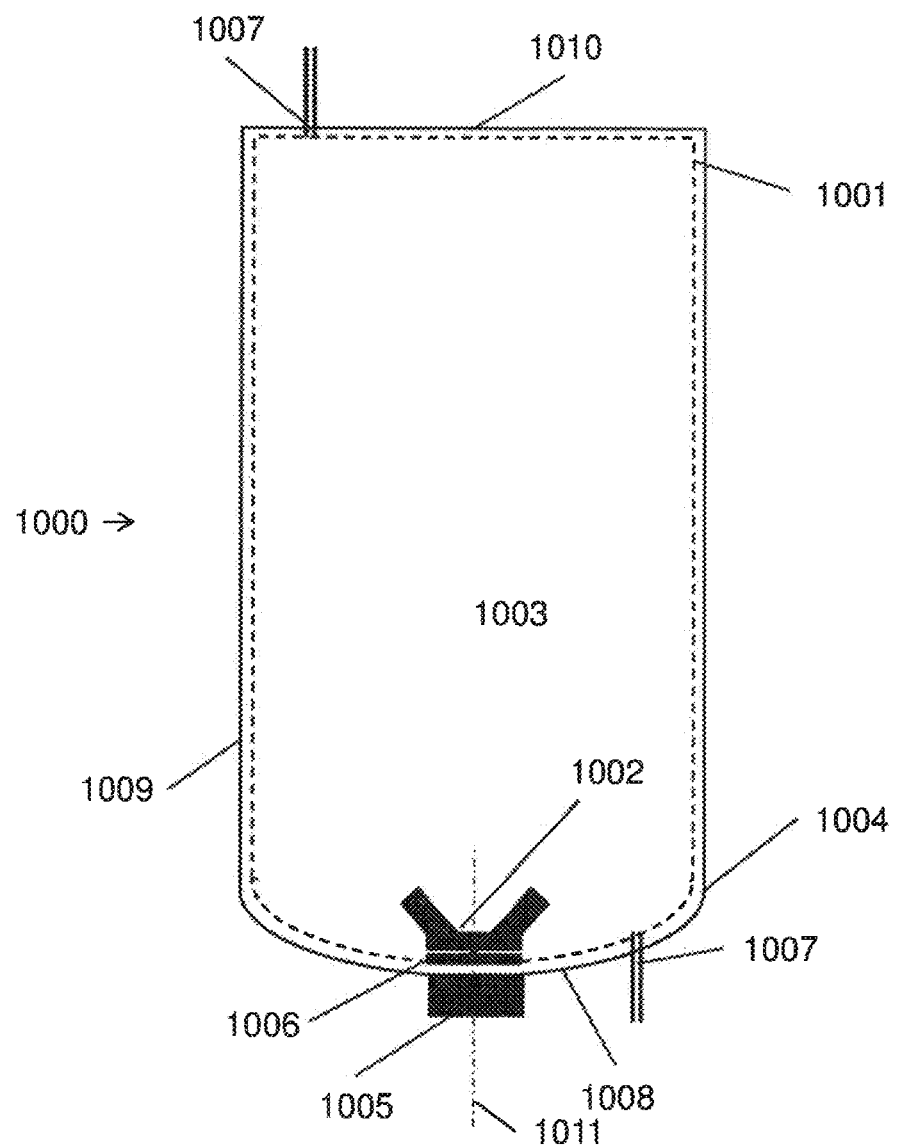
FIG. 27 illustrates a flexible bioreactor bag with a rotating magnetic impeller, mounted in a rigid support vessel with a magnetic drive.

All the embodiments disclosed are applicable to a disposable bioreactor 1000 as illustrated in FIG. 27. The bioreactor can comprise a flexible bag 1001 as the bioreactor vessel, with a magnetic impeller 1002 in an inner volume 1003 of the bag. The bag is suitably configured to be mounted in a rigid support vessel 1004, comprising a magnetic drive 1005 for the impeller, such that the impeller is driven by the magnetic drive and rotates around a central axis of rotation 1011 with a speed adequate for agitating the content of the bioreactor. The bag may comprise a receiver structure 1006 for receiving the impeller and aligning it with the magnetic drive (suitably along axis 1011), where the receiver structure may e.g. comprise a fixed shaft or a cavity capable of receiving an end of a rotating impeller shaft or part of a rotating impeller. The inner volume of the bag can e.g. be 20-5 000 liters, such as 50-2 000 liters. The bag may have one or more ports 1007 for introduction and removal of materials such as e.g. cell culture media, cell inoculates, cell culture samples, nutrients, gases and/or exhaust gas. Suitably, the bag containing the impeller is supplied presterilized, e.g. by gamma radiation sterilization. Although the magnetic drive is here shown mounted in a bottom wall 1008 of the support vessel, it may also be mounted in a side wall 1009 or a top wall 1010 of the support vessel. The impeller and any receiver structure should then be placed at a corresponding position of a bag wall.

Impellers

Figure 17:
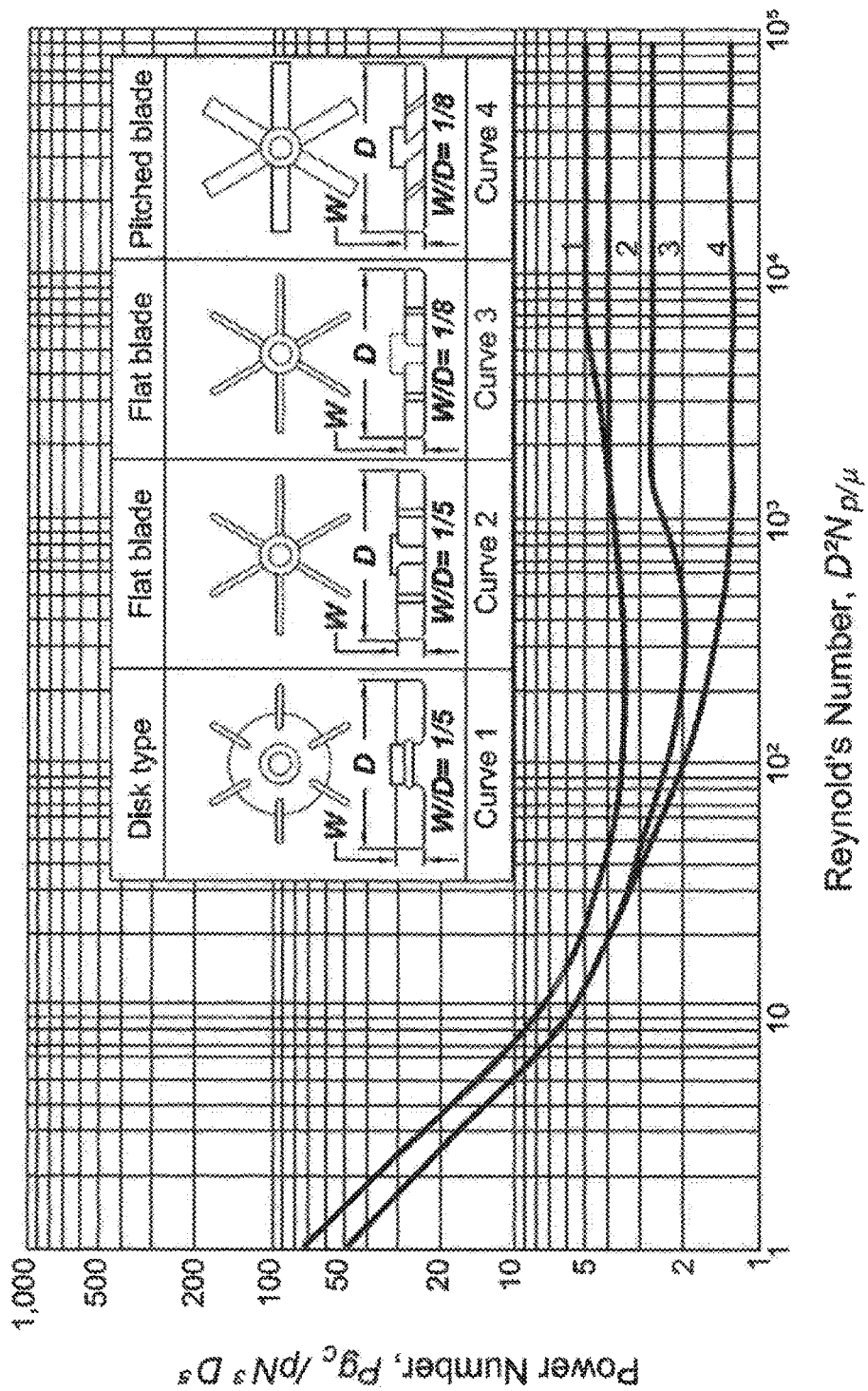
FIG. 17 is an illustration that demonstrates as the Reynolds Number decreases, a point is reached where the power number begins to increase sharply, as dependent on the type of impeller utilized.

In all the mixing/mixer system, flexible bioreactor bag and method embodiments discussed, the impeller can be a rotating magnetic impeller driven by a magnetic drive. The impeller is suitably capable of rotating around a central axis of rotation, which is suitably aligned with an axis of the drive. The impeller may rotate around a fixed shaft comprised in the system, but it may equally well comprise a shaft fixed to the impeller (or integral with the impeller) such that the shaft co-rotates with the impeller. Such a shaft may rotate in a cavity or bearing comprised in the system, typically forming a part of an impeller receiver structure. The impeller may comprise one or more mixing blades, e.g. as illustrated in FIG. 17.

Pie-Shaped Magnet Configuration

Figure 2:
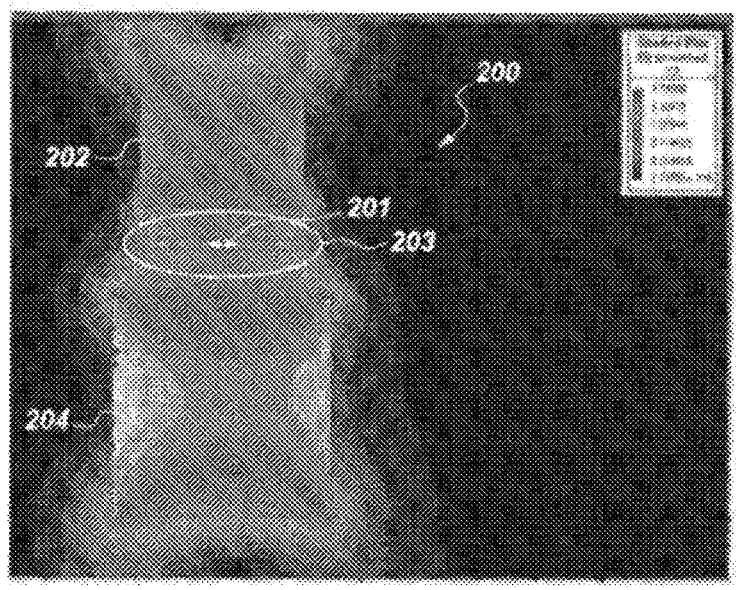
FIG. 2 (PRIOR ART) depicts a cross-sectional view of the magnetic field coupling in a prior art system.
Figure 3:
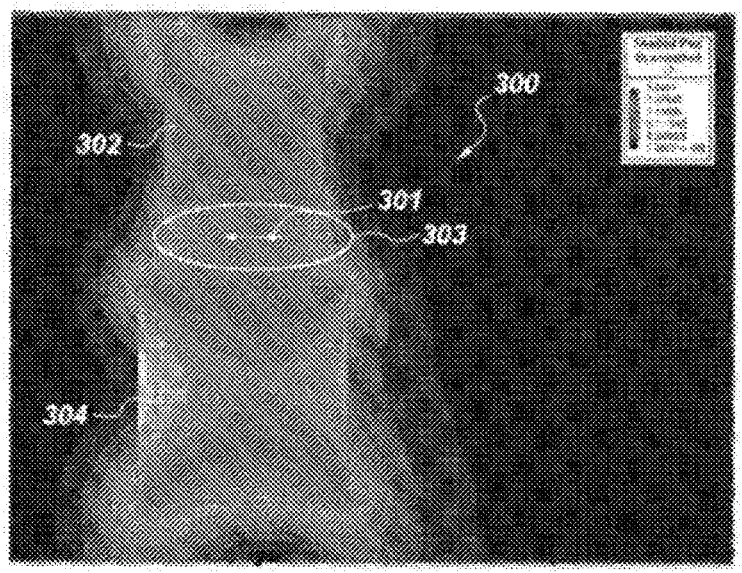
FIG. 3 depicts a cross-sectional view of the magnetic field coupling when using the individual magnet shapes and configuration as disclosed in embodiments herein.

For comparison purposes, FIG. 2 depicts a cross-sectional view of the magnetic field coupling 201 in a prior art system between a drive end magnet 204 and an impeller end magnet 202; The magnetic field density 203 is the area represented there between. An embodiment disclosed herein is shown in FIG. 3 where pie-shaped magnets are utilized in the mixer 300. A cross-sectional view shows a large increase in the magnetic field coupling 301, the increased magnetic field density 303 between the drive end magnet 304 and impeller end magnet 302.

Figure 4A:
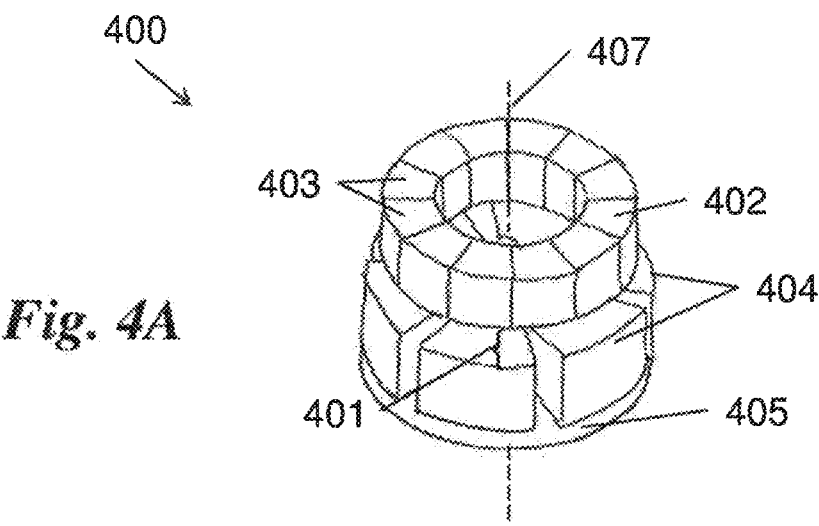
FIG. 4A illustrates an embodiment of the invention including a back iron on both ends.

FIG. 4A depicts the rotor side of a mixer 400 with a Halbach array 402 in one embodiment. The individual magnets 403 are adjacent one another without spacing to form a concentric magnetic arrangement of the Halbach array 402 around a central (rotational) axis 407. The pie-shaped drive end magnets 404 are spaced apart and positioned on a magnetic plate (back plate) 405. The magnetic plate may be a back iron, any magnetic material, including but not limited to any material of magnetic permeability greater than air. In one aspect, the magnetic plate may be a high magnetic permeability alloy such as an alloy comprising cobalt, iron, or other magnetic material. A magnetic field density 401 is created by the space remaining where the individual magnets 403 of the Halbach array 402 levitate above the drive end magnets 404.

Back Iron at Impeller and Drive Ends

Figure 4B:
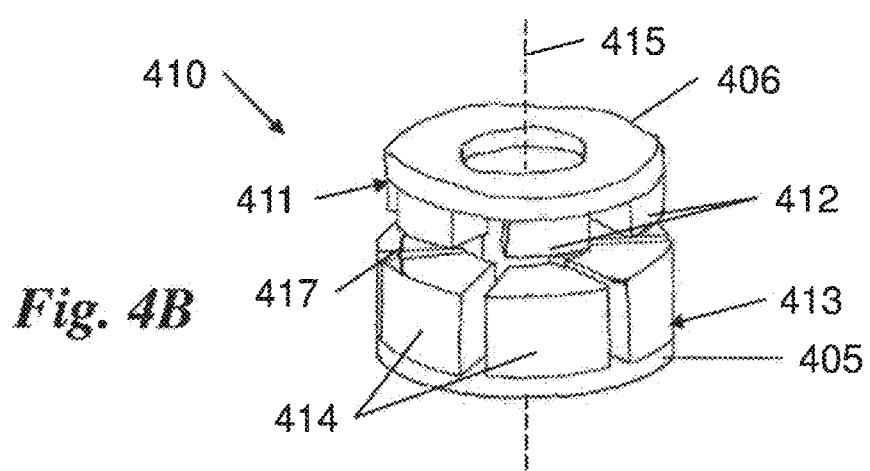
FIG. 4B illustrates an embodiment including pie-shaped magnets, individually positioned, angled, and spaced in a magnetic arrangement around a central axis.

FIG. 4B illustrates an embodiment of a magnetic drive 410 including wedged (pie-shaped) magnets 412 at a drive end 413 and wedged (pie-shaped) magnets 414 at an impeller end 411, each magnet 412, 414 individually positioned, angled, and spaced in a magnetic arrangement around a central (rotational) axis 415. A magnetic plate 405 is positioned at the impeller end 411 while a second magnetic plate 406 is positioned at the drive end 413. The magnetic plates 405, 406 are a back iron, in one embodiment, and may be any magnetic material, including but not limited to any material of magnetic permeability greater than air. A magnetic field density 417 is created between the drive end magnets 414 and impeller end magnets 412, thus increasing the magnetic coupling. In another aspect, the magnetic plate is a high magnetic permeability including materials including, but not limited to, cobalt, iron, or other magnetic material.

Figure 4C:
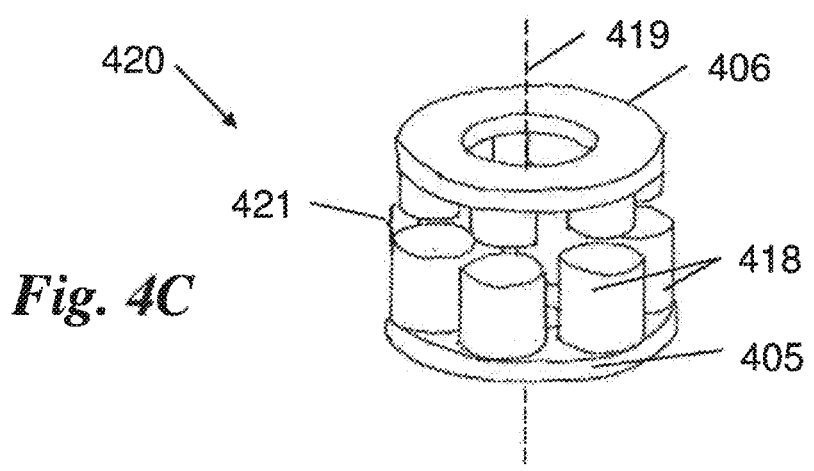
FIG. 4C illustrates the rotor side constructed with a Halbach array in another embodiment, the individual magnets adjacent one another without spacing to form a concentric magnetic arrangement.

In one embodiment, as shown in FIG. 4C, a magnetic drive 420 includes an impeller end back iron 406 and drive end back iron 405. The cylindrical shaped magnets 418 are spaced around a central (rotational) axis 419, and positioned at each end such that a magnetic field density 421 is created therebetween. The back irons enhance the magnetic coupling of the magnetic drive, thereby increasing torque.

As illustrated in FIG. 4C, back irons are placed in the drive above the impeller end magnets and below the drive end magnets. The back irons reduce the overall magnetic path in air, the magnetic field density 421, between the drive end and the impeller end magnets. As a result, the magnetic field density that couples the two ends increases.

Figure 5:
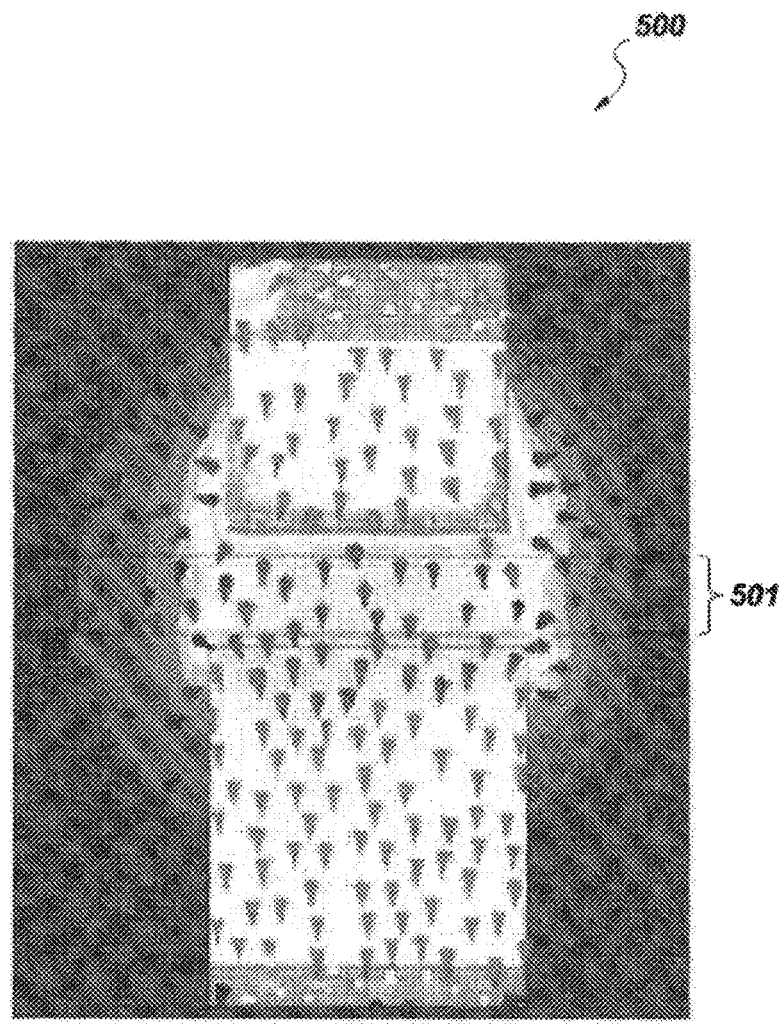
FIG. 5 depicts a cross-sectional view showing the magnetic coupling in embodiments disclosed herein when using the pie-shaped magnets and back iron.

FIG. 5 depicts a cross-sectional view of a mixing system 500 showing the magnetic coupling 501 in embodiments disclosed herein when using the pie-shaped magnets and back irons, as described in FIG. 4B.

Figure 6:
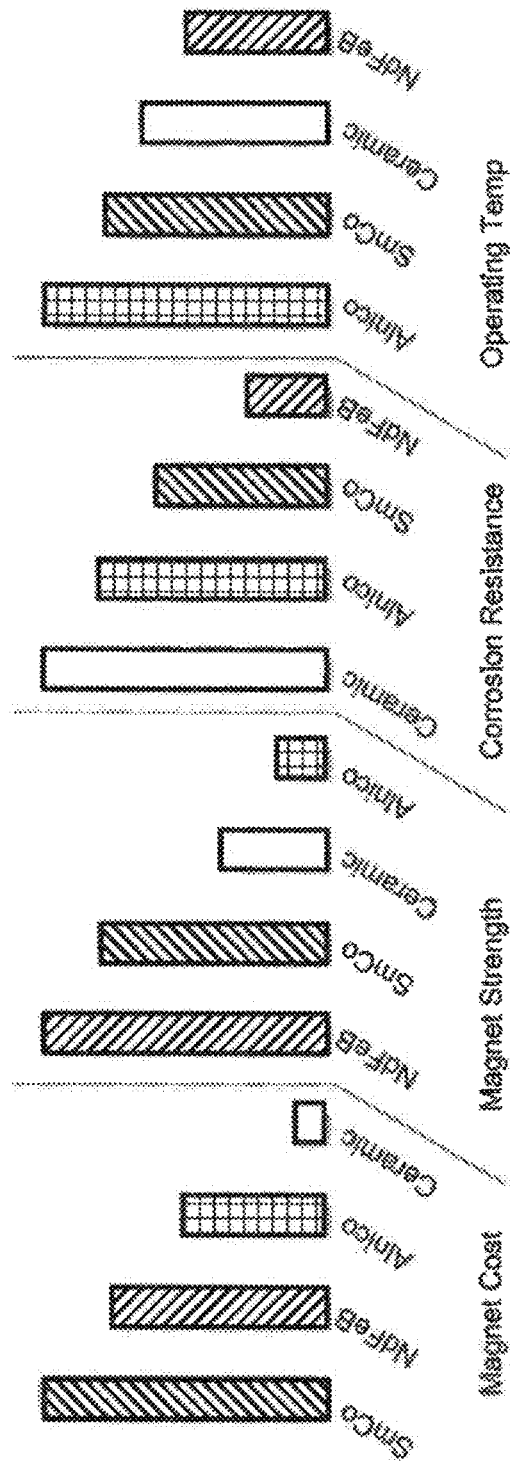
FIG. 6 provides a comparison of magnets as utilized in embodiments of the invention.

A comparison of magnets is shown in FIG. 6. Baseline torque is at about 5.8 Nm with cylindrical shaped magnets as shown in FIG. 4C.

TABLE 1

Materials used for the magnets in the magnetic drive.

| Material | | Grade | Magnet price (USD/kg) |
|---|---|---|---|
| Rare earth | Sintered NdFeB | N42SH | 70 |
| | SmCo | 28/7 | 87 |
| Non-rare earth | Alnico | Alnico 9 | 57 |
| | Ferrite | CC8B/AC12 | 8.5 |

FIG. 6 illustrates that non-rare earth magnet materials, e.g., Alnico 9 and C8B/AC12 (ceramic) are cheaper and have beneficial characteristics that align with the desired magnetic compositions, characteristics, and configurations described. Non-rare earth magnets may here and throughout the following be defined as magnets comprising less than 5 wt % of rare earth elements, such as less than 1 wt % of rare earth elements. Rare earth elements comprise elements of the lanthanide series (i.e. the elements with atomic numbers 57-71) as well as scandium and yttrium.

Figure 7:
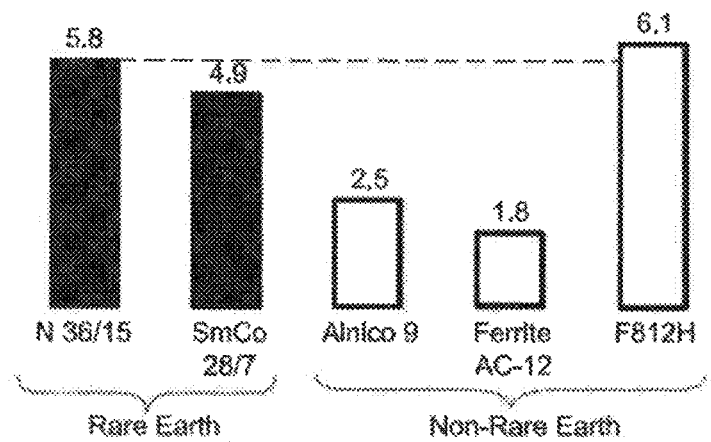
FIG. 7 depicts a comparison of maximum torque for cylindrical magnets using different materials in one embodiment.

FIG. 7 is a comparison of maximum torque for cylindrical magnets ($\phi=0.75 \times 0.75$). By replacing Neodymium (Sintered NdFeB) magnets, and using other non-rare earth magnets, while keeping the cylindrical shapes and arrangement, the torque production is greatly reduced.

Figure 8:
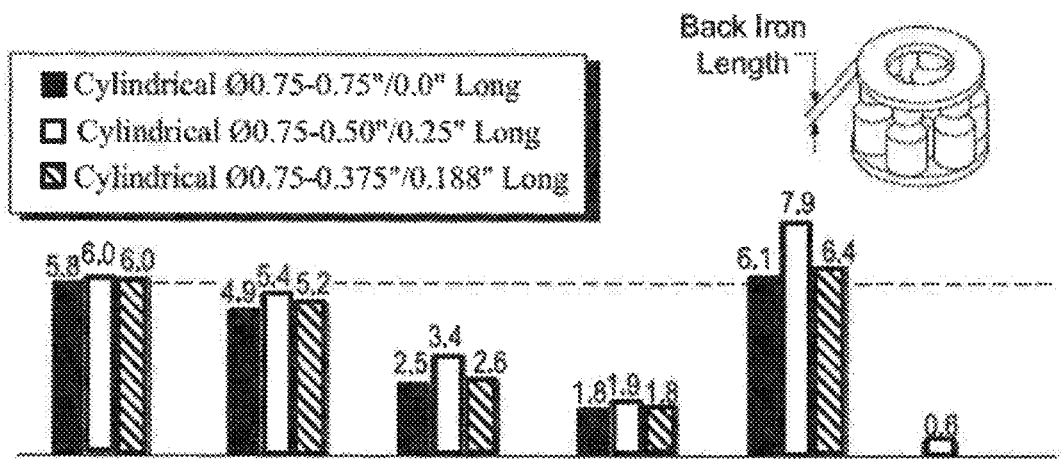
FIG. 8 depicts a comparison of maximum torque for cylindrical magnets with back iron.

In one aspect, a back iron may be added on one of the impeller end or the drive end. The back iron added at impeller and drive ends improves torque production, as illustrated in FIG. 8. Specifically, FIG. 8 demonstrates the comparison of maximum torque for cylindrical magnets with back iron, as represented in FIG. 4C. FIG. 8 shows that maximum torque produced by different types of magnets (e.g., N 38/15, SmCo 28/7, etc.) as a function of magnet geometry. The ferrite magnet grade FB12H gives twice the amount of the torque produced without the back plate, while eliminating the use of rare earth magnets. Three of the magnet grades are not able to produce the baseline torque of the rare earth magnets.

Figure 9:
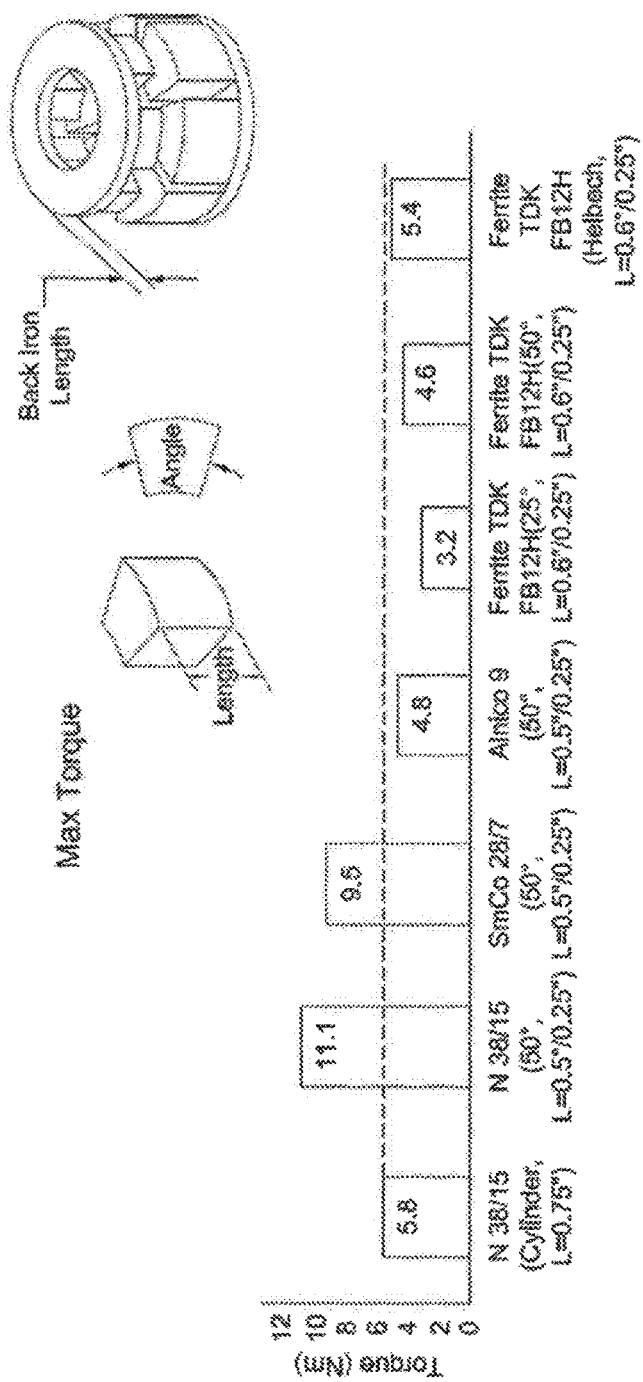
FIG. 9 depicts a comparison of maximum torque for pie-shaped magnets and Halbach array

Embodiments of the invention modify the shape of the magnets from cylindrical to pie-shaped configurations. As shown in FIG. 9, the improved impeller-drive design provides 2.5 times the torque without the need for expensive Neodymium magnets. Ferrite magnet grade FB12H gives 2.5 times the amount of torque produced without the back plate and the magnet pie shape. As demonstrated in FIG. 4B, and referenced in FIG. 9, a comparison is shown of maximum torque for pie-shaped magnets.

Halbach Magnet Array

As shown in FIG. 9, an embodiment of the Halbach impeller-drive design of FIG. 4A provides the desired torque without the need for expensive Neodymium magnets. This arrangement of Halbach array and pie shaped magnets increases the torque produced by a factor of 3 which delivers the baseline torque.

Axial Flux Stator

Figure 11:
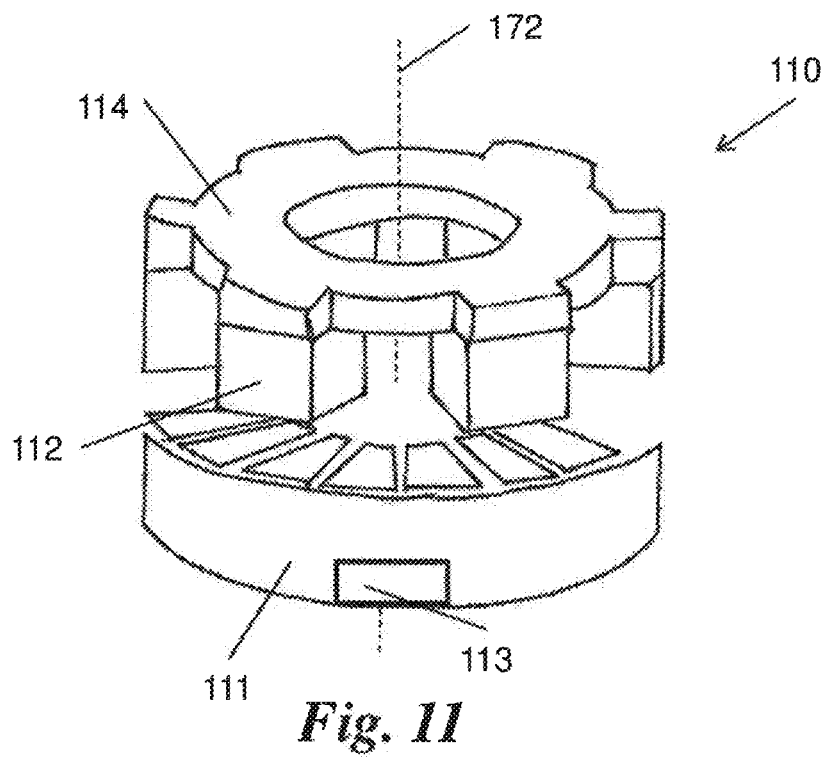
FIG. 11 illustrates an embodiment of the invention from a perspective side view.

Embodiments of the invention provide an axial flux stator to reduce the drive end size, as well as reducing the number of components, and increase its reliability. FIG. 11 depicts an embodiment of the axial flux stator 110 without the shaft and bearing, and without the lever mechanism as utilized in the prior art. The drive stator 111 is positioned on an underside of the magnets 112 of the impeller end 114, aligned along a central axis of rotation 172, and has a control circuit 113.

The electrical and mechanical components of the axial flux stator 110 are adjusted to address challenges in the modified design. In embodiments of the axial flux stator, the electrical components comprise: high current density (cooling), a higher number of slots to allow high count of slots per pole and hence the ability to choose various coil span (to suppress harmonics), longer slots resulting in higher leakage inductance and lower power factor, and higher current results in higher flux thus accommodating a bigger stator tooth to avoid saturation.

Figure 12:
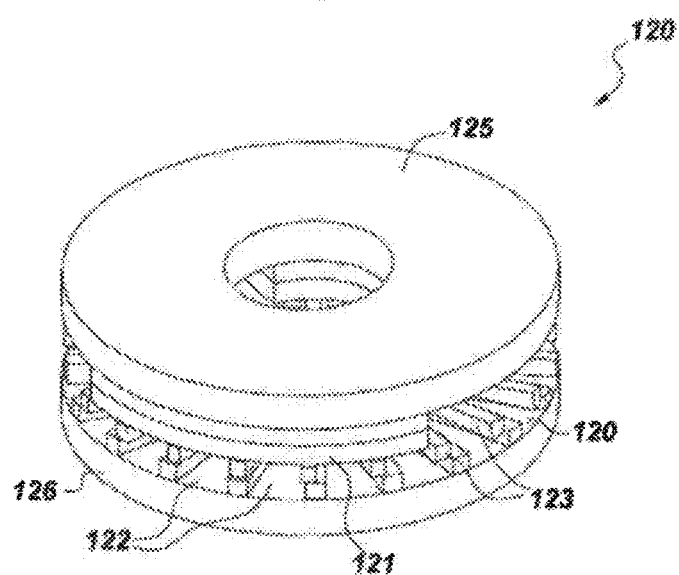
FIG. 12 illustrates an embodiment of the invention from a perspective side view.

The construction of an axial flux stator 120 is depicted in FIG. 12 as an axial-type magnetic gear. A magnetic core 121 is here shown positioned between a high-speed rotor 125 (stator with high frequency) and a low speed rotor 126. The magnetic core 121 has a number of slots 122 depending on the arrangement of the impeller magnets and windings. The magnetic core may be laminated, powder type, or a taped core, as desired. A set of windings are shown in FIG. 12 as stationary steel segments 123, or stator teeth, with modulation slots 122. The set of windings may be tooth-wound, distributed, or fractional windings, as well. Windings can also be single or multi-layer, wave or lap windings, full or short pitched windings. The stationary steel segments can have additional slotting to accommodate magnetic gearing (e.g., Vernier type machine) with single or multi-stage gearing. The stator can also have additional magnets when using a Vernier type machine.

Figure 13A:
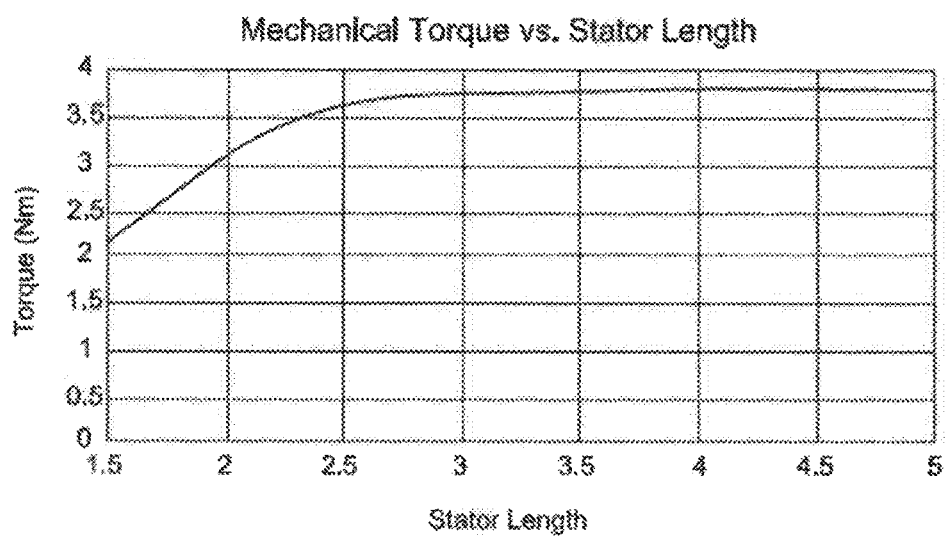
FIG. 13 (a), (b), (c) shows analyses of varying the stator length.
Figure 13B:
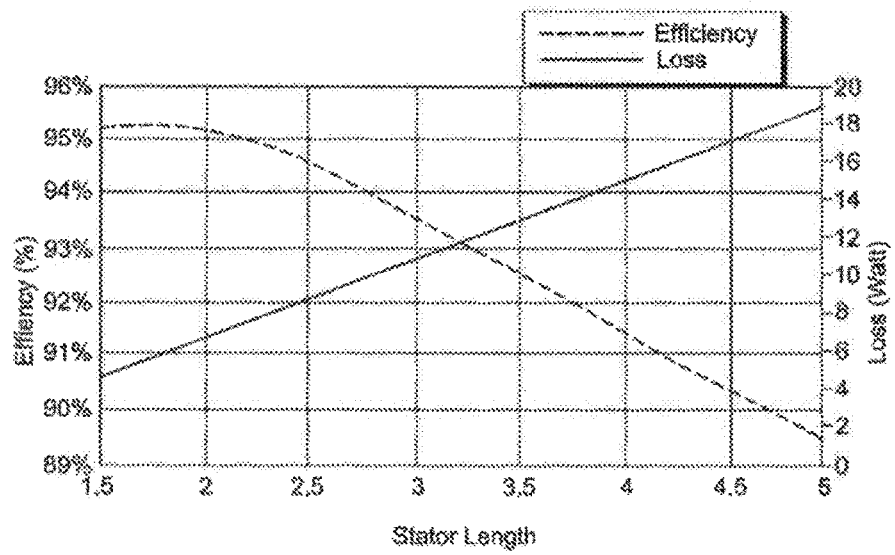
Figure 13C:
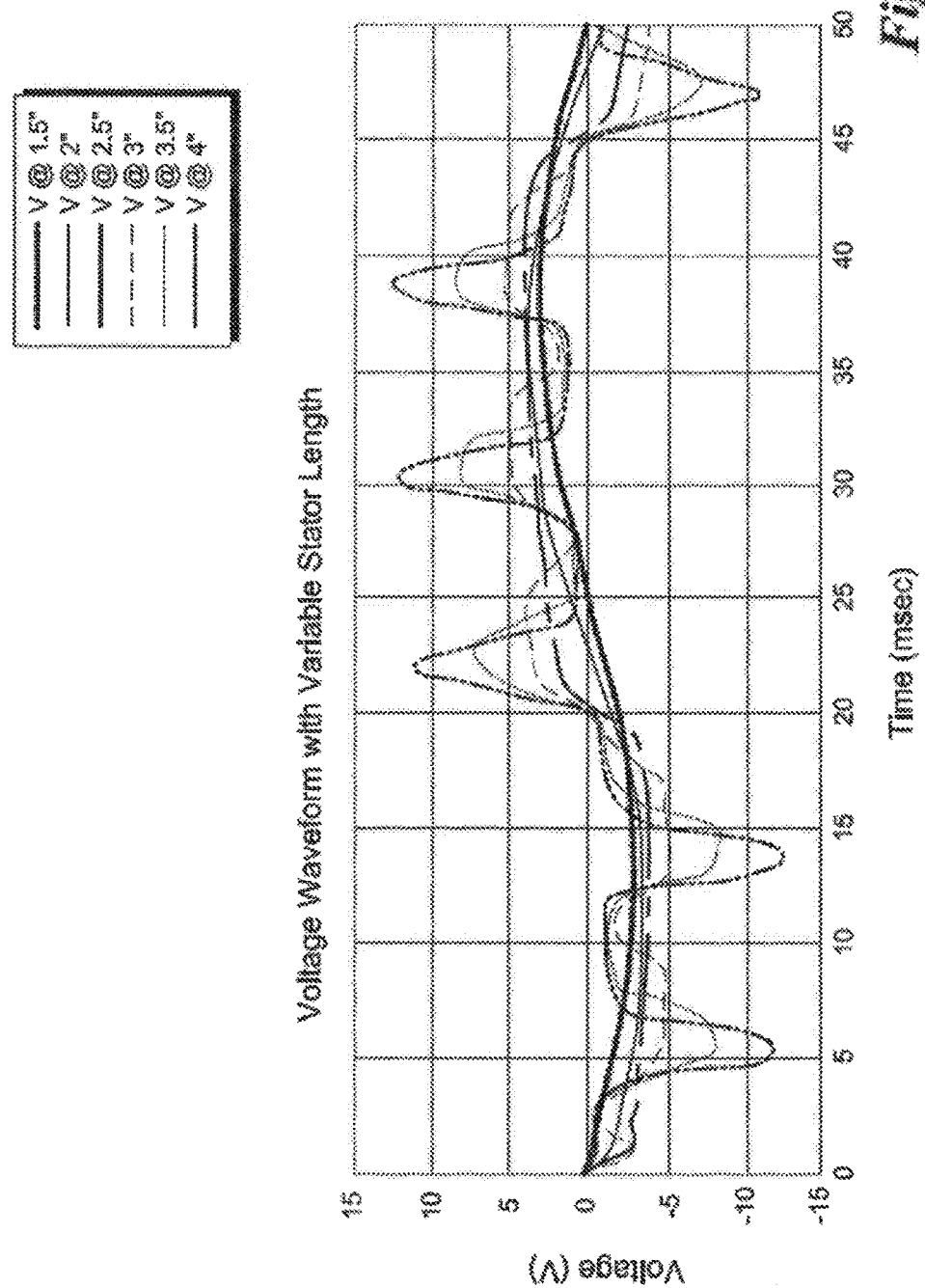
Figure 14A:
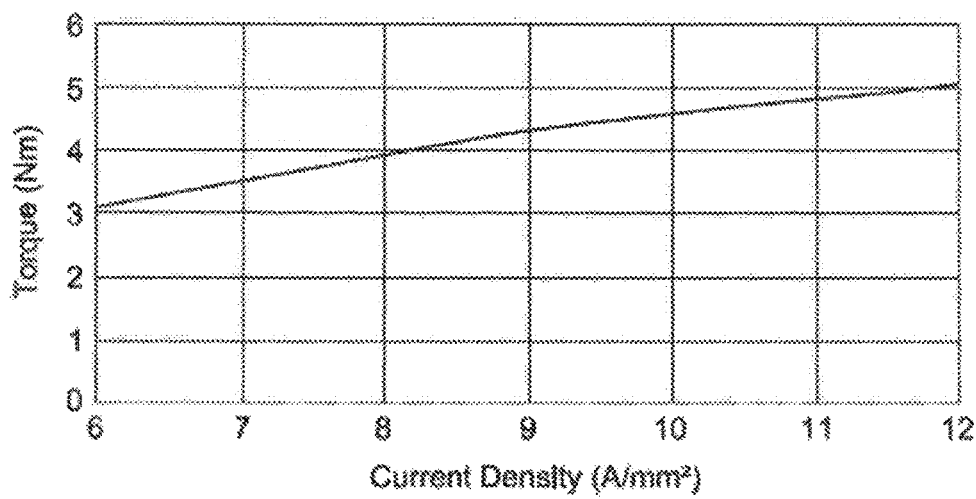
FIG. 14 (a), (b), (c) shows an analysis of varying the current density.
Figure 14B:
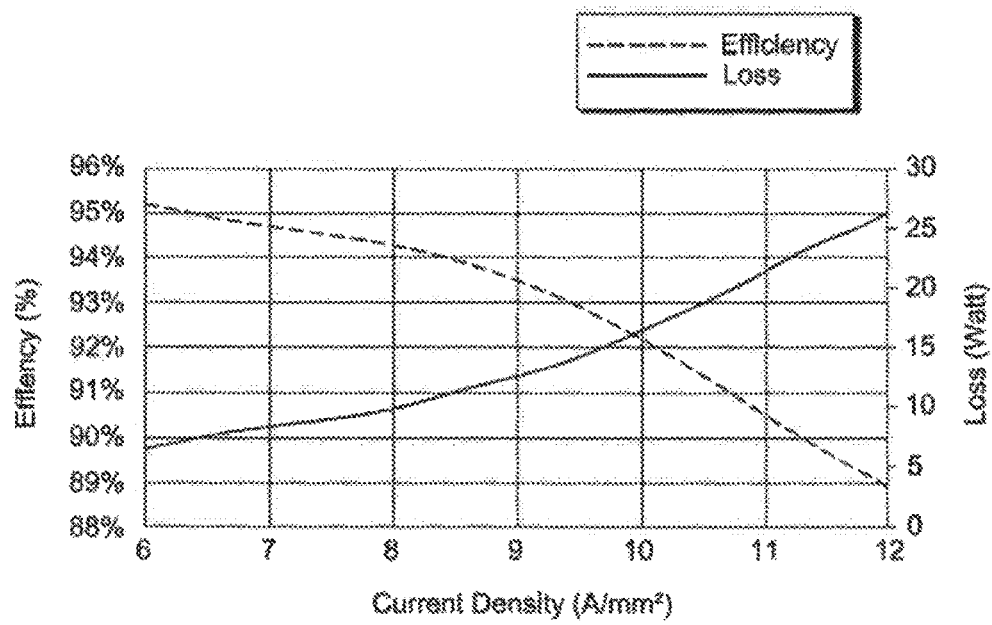
Figure 14C:
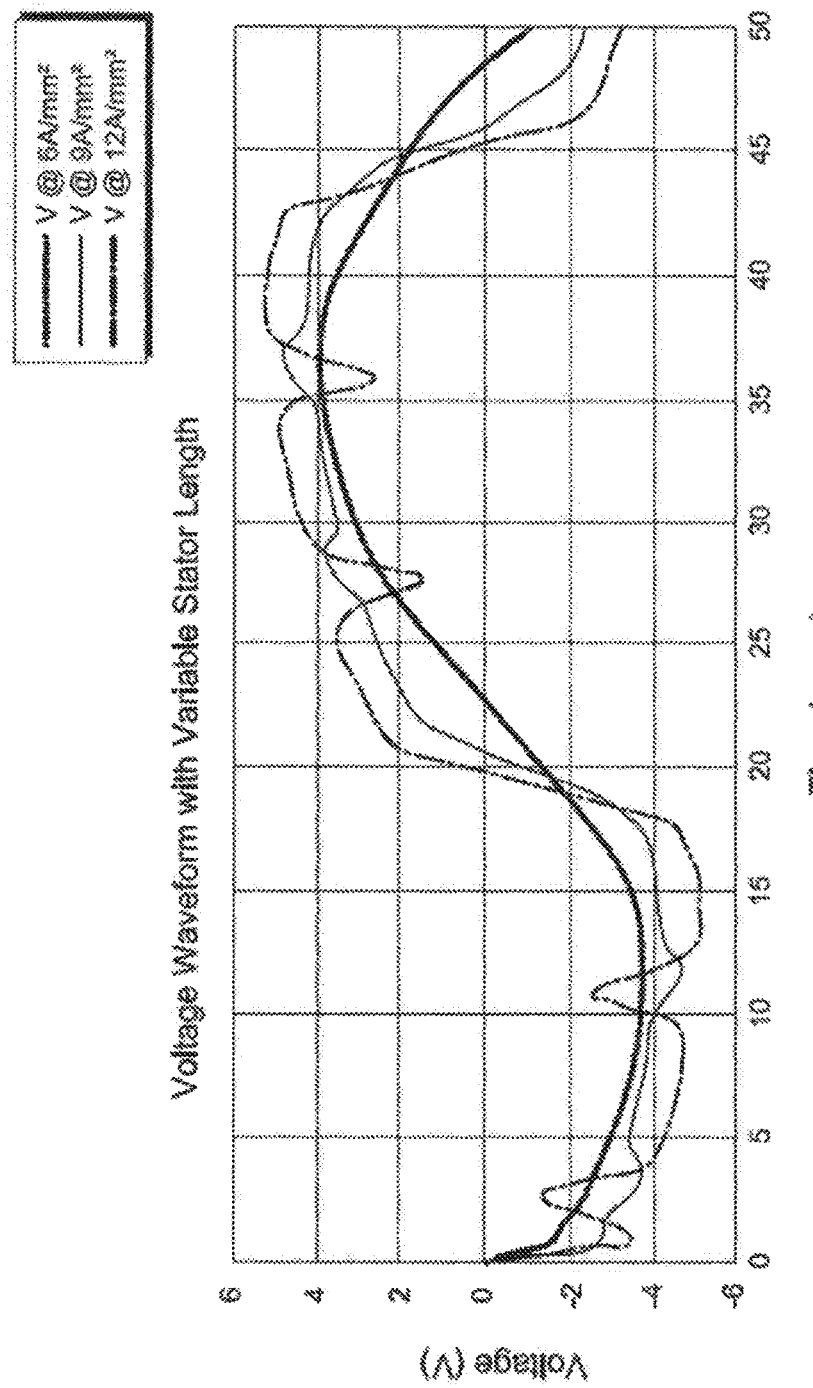
Figure 15A:
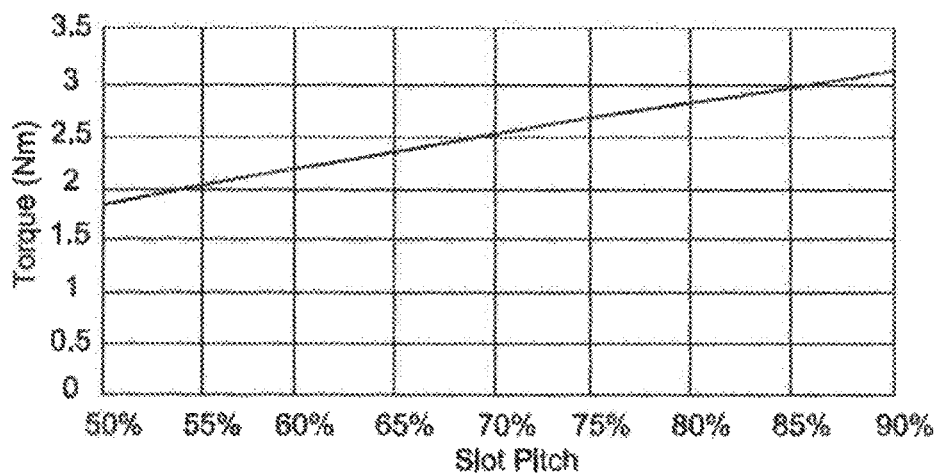
FIG. 15 (a), (b), (c) demonstrates analyses of varying the slot pitch, and resulting torque.
Figure 15B:
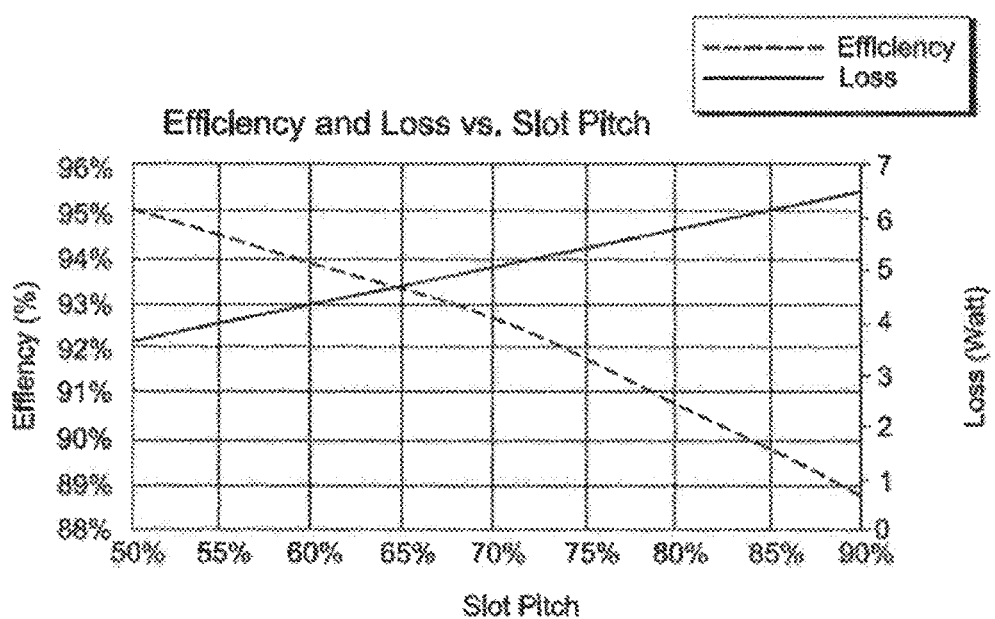
Figure 15C:
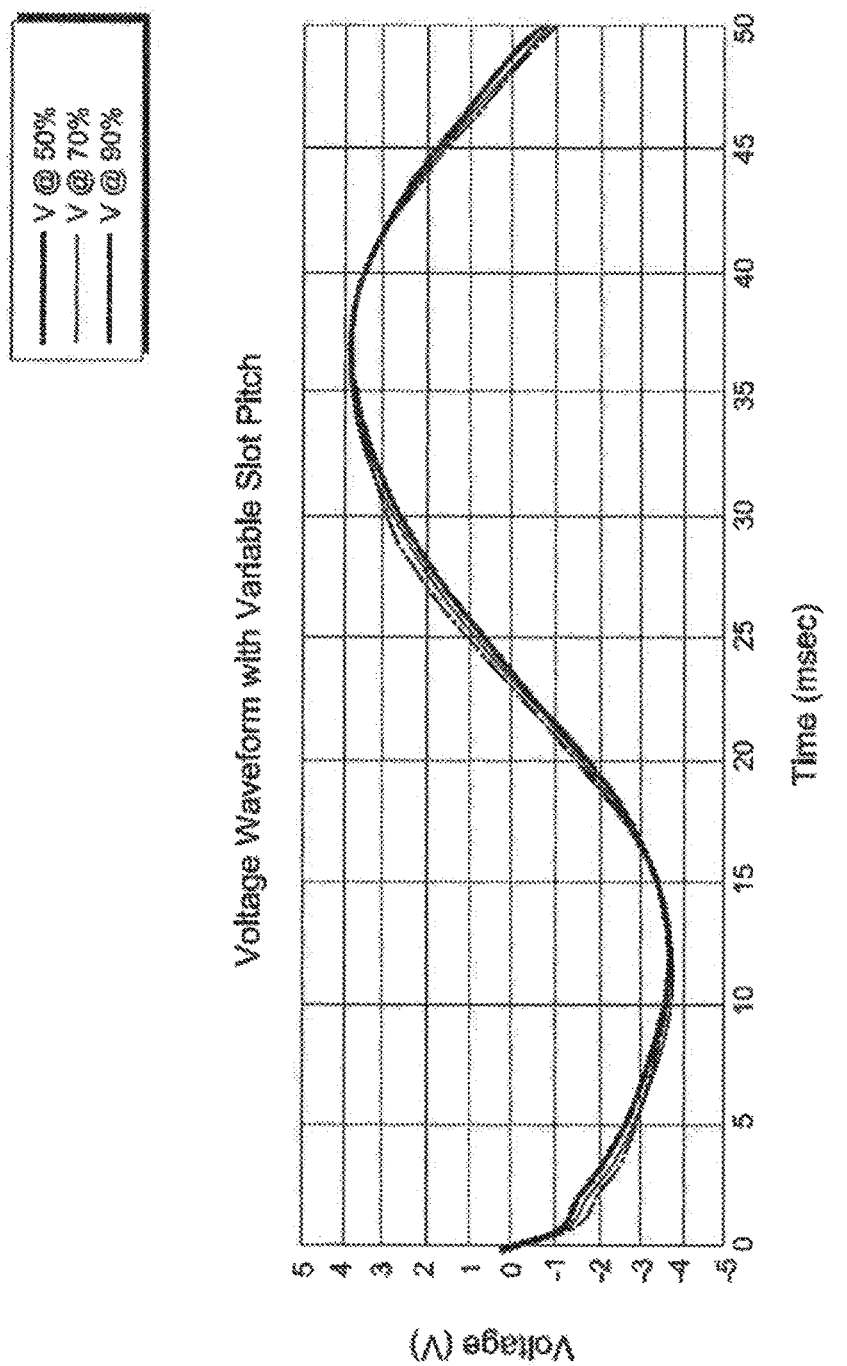

An analysis of the axial flux stator with distributed windings (e.g., an eighteen-slot example) demonstrates that by increasing the stator length, a higher current path results per slot; saturation of the teeth occurs and causes increased harmonics (See FIG. 13). Increasing the stator current density results in higher torque; again, saturation of the teeth occurs and causes increased harmonics (See FIG. 14). And, by increasing the stator slot pitch, higher torque results while placing mechanical constraints on the innermost tooth width (See FIG. 15).

Figure 16A:
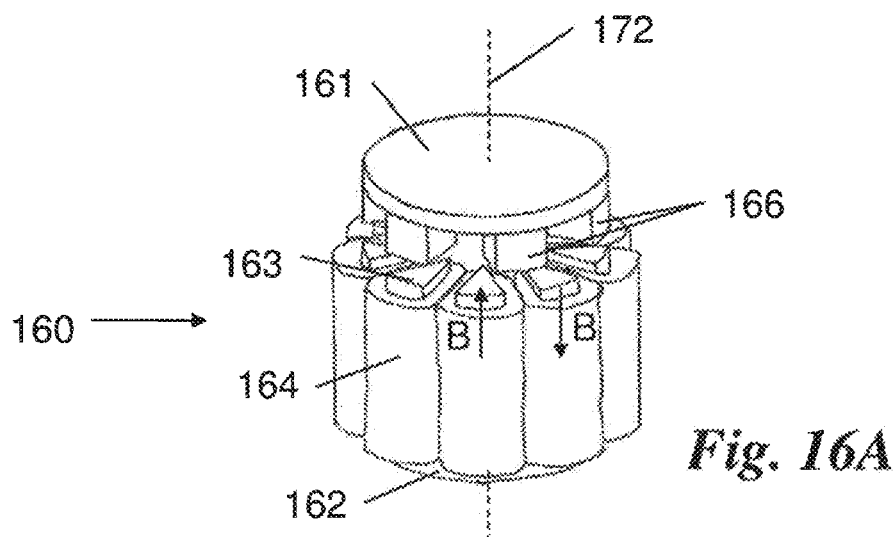
FIG. 16A illustrates a perspective view of an embodiment of a tooth wound axial flux stator.
Figure 16B:
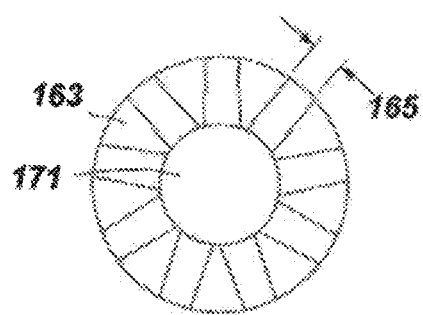
FIG. 16B depicts a perspective top view of the axial flux stator of FIG. 16A.
Figure 16C:
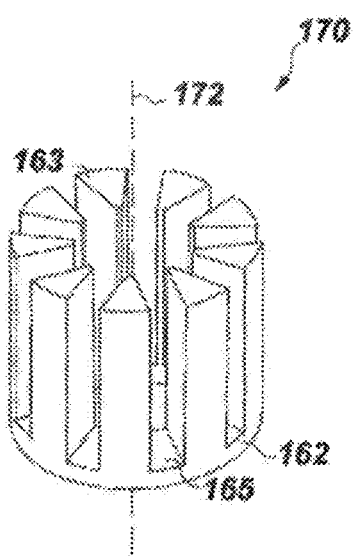
FIG. 16C depicts a perspective side view of the axial flux stator of FIG. 16A.
Figure 16D:
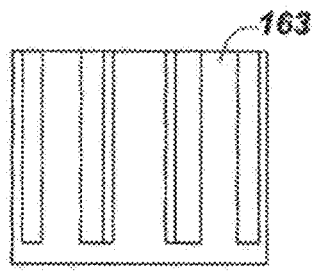
FIG. 16D depicts a perspective side view of the tooth height of the axial flux stator of FIG. 16A.

FIG. 16A illustrates an embodiment of a tooth wound axial flux stator 160 with nine (9) slots 165 (See FIG. 16C), for exemplary purposes, and not limitation. FIGS. 16B, 16C, and 16D depict perspective views to more clearly illustrate the details of the axial flux stator 160. The stator core comprises pie-shaped magnetic stator teeth 163 that extend vertically from the stator back iron 162. The stator core 170 can be formed from sintered powdered iron, ferrite, or machined from a coil of magnetic steel. Conductive windings (current carrying elements) 164 are wound around the stator teeth 163. The conductive windings are divided up into phases. Within each phase winding, the sense, field direction, of the individual coils alternates so that the application of phase current to the phase winding creates a magnetic field that is directed vertically upward in one tooth and vertically downward in another tooth. The flow of current through the conductive windings forms a magnetic field that flows through the stator teeth, across the air gap between the stator 160 and a rotor 161 capable of rotating around central axis 172, interacts with the magnets 166 on the rotor, travels through the rotor 161, and returns through a rotor magnet of opposite magnetic polarity, across the air gap between the stator and rotor, through an oppositely-excited stator tooth, closing through the stator back iron 162.

As shown in FIG. 16B, the exemplary stator has nine slots 165 of width of about 0.470 in (1.2 cm); the inside diameter (a hollow core 171 with central axis 172) of the stator core 170 is about 1.575 in (4.0 cm), and the outside diameter of the stator core is about 3.250 in (8.25 cm). The width of the slots, the core inside diameter, and core outside diameter are parameters that determine the performance of the motor. FIG. 16C depicts the magnetic stator core 170 including stator teeth 163 in combination with the base back iron 162 and shows that the stator core is about 2.750 in (7.0 cm) height, but can vary in size, shape and dimension, as desired for a particular mixer. FIG. 16D depicts the height of the magnetic pie-shaped stator teeth 163, the height of which is shown here as about 2.500 in (6.35 cm). The height of the stator teeth and the thickness of the stator back iron are additional parameters determined during the design of the stator, and so may be varied in shape and dimension.

Figure 16E:
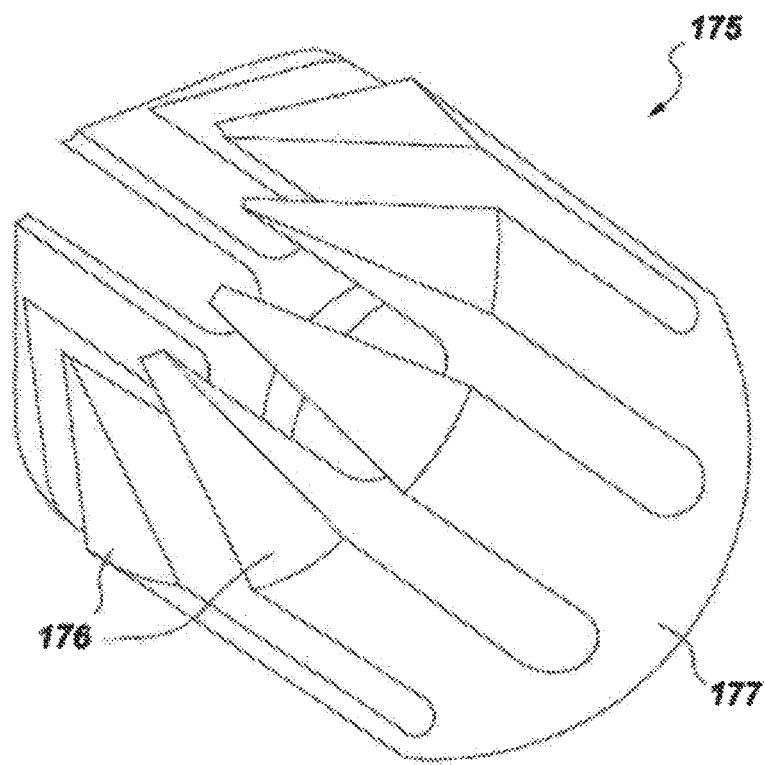
FIG. 16 E depicts an embodiment of a stator core described herein.

In one embodiment, as shown in FIG. 16E, the stator core 175 is defined with conic teeth 176 and including a back iron 177. As such, the stator core may be modified and designed to provide operational efficiency of a mixer.

Figure 10:
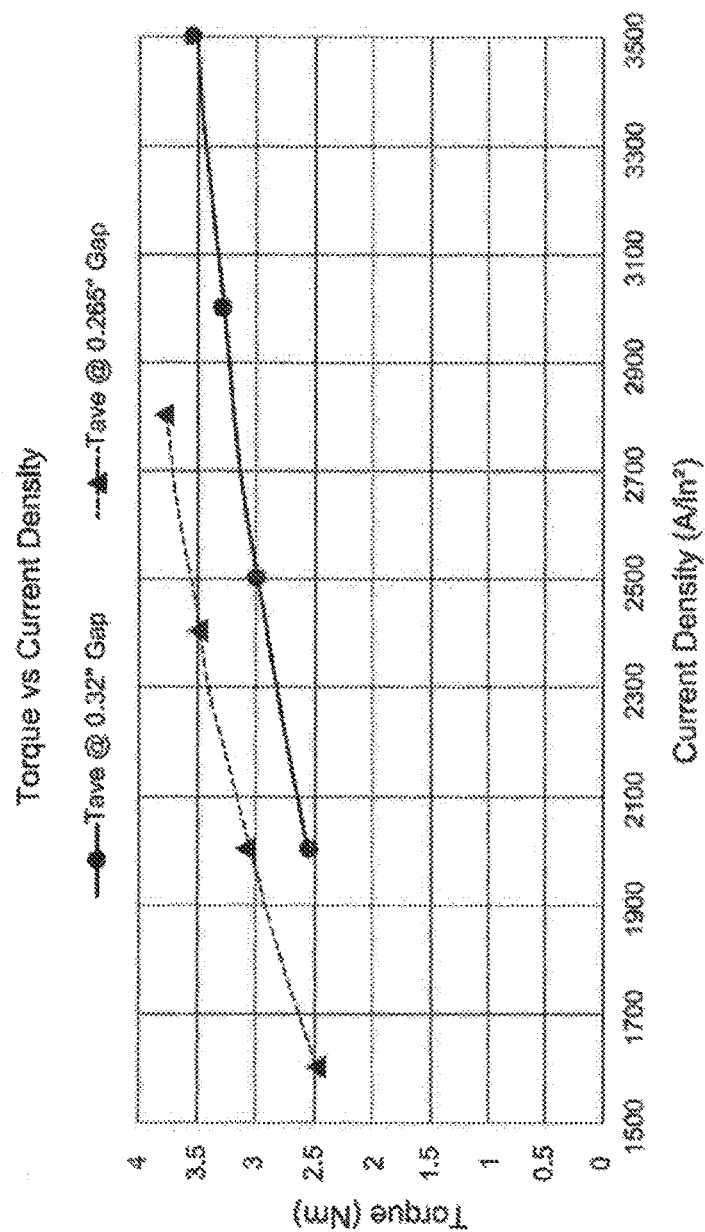
FIG. 10 depicts a graphic illustration of the relationship of torque versus current density for the axial flux stator in one embodiment.

FIG. 10 compares torque versus current density of the axial flux stator 160 for gaps of about 0.32 inches (0.81 cm) and about 0.265 inches (0.67 cm) between the stator and rotor. More torque is produced for a given current density with the smaller gap. The efficiency is slightly greater for the smaller gap since the current is smaller.

As demonstrated, the embodiments thus described address the problems presented in the art. The cheaper impeller as described comprises a magnetic coupling improved by increasing the magnetic field density. Higher torque density is produced by optimizing the impeller magnet by way of material, shape, and back iron, individually or in combination. The rare earth magnets can be replaced by less expensive and environmentally friendly non-rare earth materials, such as Alnico and Ferrite, for example. In addition, the large and oversized drive assembly used prior now can run a much smaller impeller. Further, the moving parts on the drive side, near the user have been repositioned to provide a safer device overall.

Additional technical and commercial advantages are provided with the more reliable system that includes the axial flux stator; the axial flux stator has a smaller drive, no moving parts, and reduced magnetic force during bag installation. While cost and availability of the magnets is an advantage with improving magnet shape and material, the efficiency of the magnetic coupling that increase torque is very useful for further intensification of the bioreactor, various mixing systems, and overall efficiency.

In use, for example, microbial fermentations utilize more agitation for sufficient mixing, gas mass transfer and heat transfer at the reactor wall. An improved device of the invention including the axial flux stator improves user experience due to a less complex design. Not only is the design more compact than a drive with permanent magnets, but the installation and removal of the bag is improved as there are no permanent magnetic forces that have to be overcome. Moving parts are avoided with consequences on machinery directive requirements, sealing and ingress protection to avoid prior standard design that utilized a lever mechanism to separate the drive from the impeller such that the bag can be pulled out of the reactor bottom end piece.

Various embodiments will be better understood when read in conjunction with the appended drawings. It should be understood that the various embodiments are not limited to the arrangements and instrumentality shown in the drawings.

Torque produced in the mixing process relates to different fluid properties such as viscosity and density. Torque also relates to different mixing conditions such as presence of obstacles and changes or issue with gas sparging. For example, disruption of the continuous liquid or sparger liquid by zones of air presents large bubbles or channels, a behavior typically called [gas] flooding of the mixer; this leads to a drastic reduction of power input. A torque measurement (i.e. a continuous measurement in real time) under conditions close to or at the point of flooding of the mixer allows for better process control and higher utilization of mixing power, including improved capacity and capability in the process step. For example, a bioreactor could operate at higher mass transfer and thus higher productivity. Moreover, torque measurements, along with speed, enable determination of power transmitted to fluid by actual measurement, in contrast to using solely empirical impeller power number and speed, and thus allow actual mass transfer determination (i.e., gas transfer calculations). As described herein, embodiments refer to a torque and speed sensor, such as a transducer, and a method of using the measured torque and speed to detect the different fluid and mixing properties, conditions, and abnormalities.

Mixing Power

Embodiments of the invention disclosed allow the power consumed by a rotating impeller to be easily measured in a process fluid. The units express this power as 'horsepower' (HP). Mixer performance relates to horsepower; problems, however are associated with this tendency. In general, Power (P) input to the fluid can be calculated for typical mixers (turbulent flow) applications as follows:

$$P = \frac{\rho N_p N^3 D^5}{g_c} = \text{Specific Gravity} \quad \text{(Eq 1)}$$

$N_p$ = Power Number of Impeller $N$ = Impeller Speed $D$ = Impeller Diameter $g_c$ = dimensional constant Viscosity Effect As viscosity increases, the impeller power number may begin to increase. This becomes important in the HP calculations because as power number begins to go up so does the horsepower utilized to drive the mixer. Simply increasing the input [horse-] power may be the answer, but this change reduces the service factor of the mixer drive, hence a 'bigger' mixer may be required. Viscosity increase also affects the flow characteristics of fluid as compared to water.

Reynold's Number

Reynolds Number is a dimensionless number that can be derived as follows:

$$N_{re} = \frac{D^2 N \rho}{\mu} \quad \text{Eq (2)}$$

$\rho$ = Fluid Density $\mu$ = Viscosity

The power number ($N_p$) is constant for each impeller type, as long as the Reynolds number is sufficiently high. The power number is a function of Reynolds Number ($N_{re}$).

The illustration of FIG. 17 shows how the power number for each impeller varies with changes in Reynolds Number. As the Reynolds Number drops, a point is reached where the power number begins to increase sharply. This point depends on the type of impeller in use. Reynolds Numbers or $N_{re}$ between 1000 and 2000 are generally considered "in transition".

Figure 18:
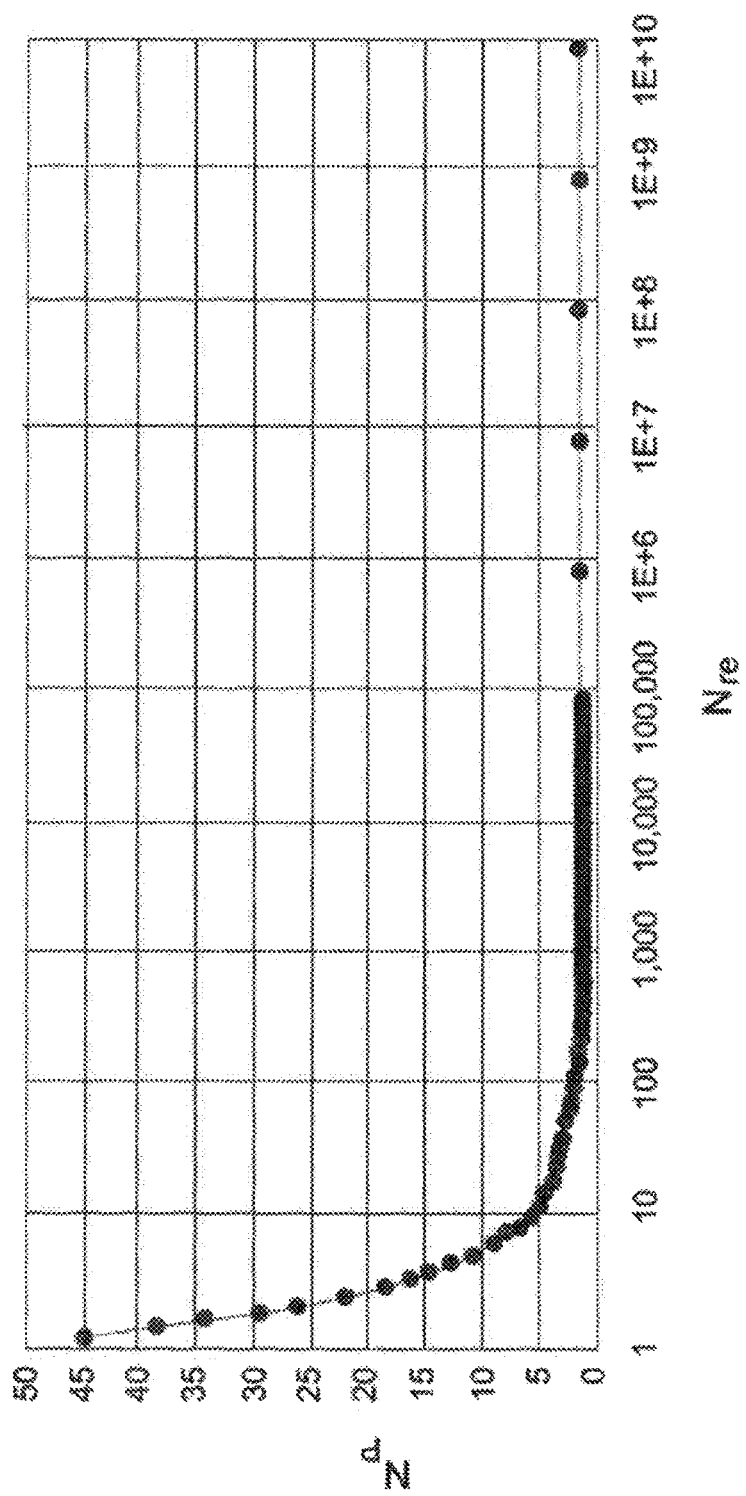
FIG. 18 charts power number, $N_p$, versus Reynolds Number, $N_{re}$.

The Reynolds number is the indicator of the type of mixing fluid in which the mixer will operate. If the Reynolds Number is above 2,000, the power number is constant, When the Reynolds Number calculated is less than 1,000 (i.e., laminar flow), then the power number increases as the Reynolds Number decreases. Consequently, the shaft horsepower calculated is based on the corrected power number. In this case, as shown in FIG. 18, a power number ($N_p$) vs Reynolds Number ($N_{re}$) curve is obtained from the impeller manufacturer or by experimentation.

In embodiments of the invention, the power utilized to mix a fluid at a given speed can vary based on multiple parameters, including but not limited to: (i) the impeller diameter, (ii) the impeller blade design, (iii) the fluid properties (i.e. viscosity and density). In some applications, such as mammalian cells mixers, controlling the power delivered to the fluid is an element of the mixing process. Since the mixing power is driven by the drive system, it can be measured and controlled from that side. The drive system can be in the form of a stator that rotates the impeller, or a set of magnets coupled to the impeller magnets and driven by a separate motor. In these embodiments, the magnetic field that couples the drive to the impeller depends on the power (and also torque) delivered to the impeller. By measuring the magnetic field or flux, the torque, speed, and power delivered to the impeller can be calculated and hence controlled. Further, the current and voltage inputs to the drive system are related to the power delivered to the system. These values can also be used to calculate the power delivered to the impeller.

Characterizing a Fluid

Fluid properties of density p and viscosity μ play a role in specifying the desired mixing power and torque, as these properties are represented in the Reynolds number calculation as well as in the specific power equation. In estimating such parameters, for exemplary purposes, and not limitation, curve #4 from the FIG. 17 is shown in FIG. 18.

Next, the torque-speed curves are plotted for seven different fluids: water, and six other fluids with different density, dynamic viscosity, or combination of both, than water. Table 1 shows the general properties of each fluid (at 25° C.) while Table 2 shows the impeller and tank properties.

TABLE 1

| Property | Water | Fluid #1 | Fluid #2 | Fluid #3 | Fluid #4 | Fluid #5 | Fluid #6 |
|---|---|---|---|---|---|---|---|
| Fluid Density, ρ [kg/m³] | 1000 | 1000 | 1000 | 1000 | 1100 | 1300 | 1500 |

TABLE 1-continued

| Property | Water | Fluid #1 | Fluid #2 | Fluid #3 | Fluid #4 | Fluid #5 | Fluid #6 |
|---|---|---|---|---|---|---|---|
| Dynamic Viscosity, μ [Pa · s] | 0.00089 | 0.0089 | 0.089 | 0.89 | 0.00089 | 0.00089 | 0.00089 |

TABLE 2

| Property | Value |
|---|---|
| Impeller Diameter [in] | 3.5 |
| Tank Volume [Lit] | 200 |

Figure 19:
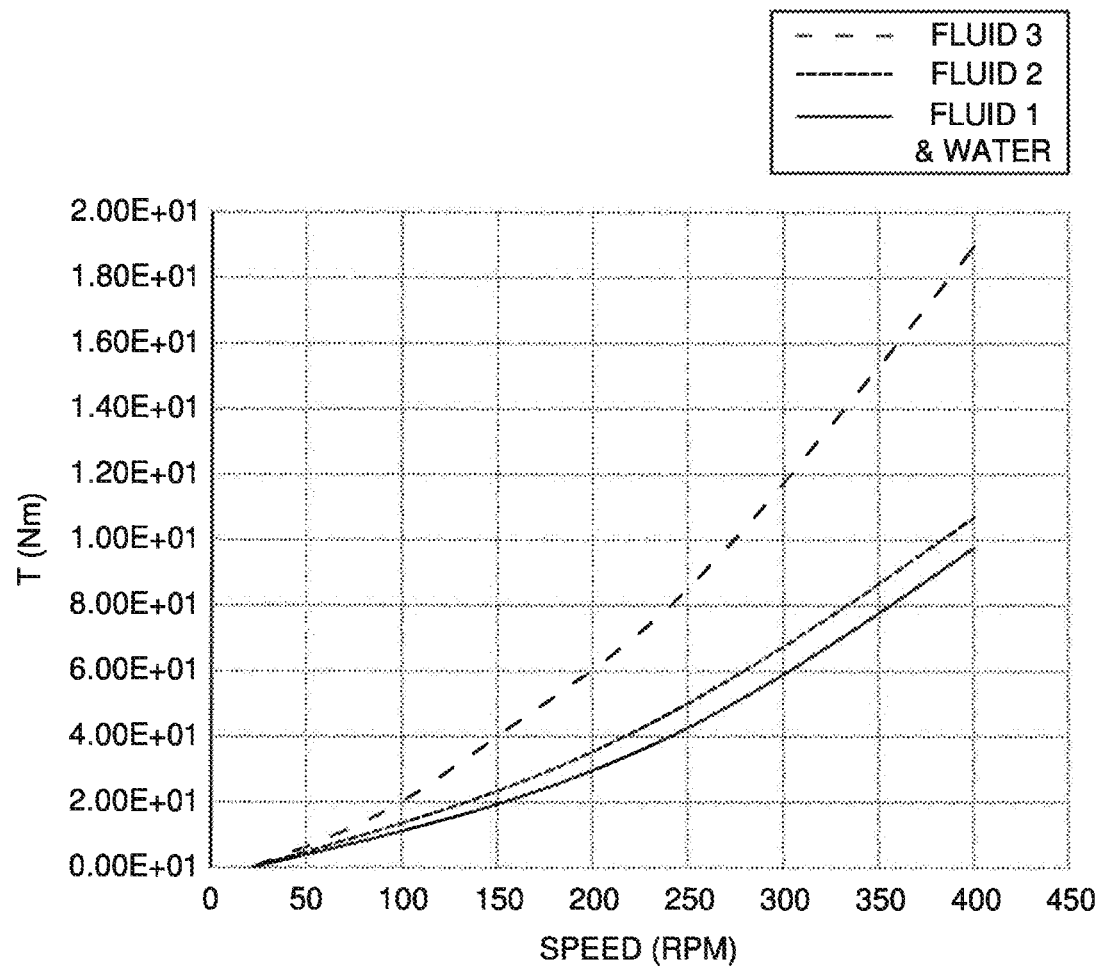
FIG. 19 depicts the variation of impeller torque as a function of rotating speed for Fluids 1, 2, 3, and water.

The calculation for the torque-speed characteristics are done using equation 1 (Eq. 1) and equation 2 (Eq. 2). FIG. 19 shows the variation of impeller torque as a function of rotating speed for Fluids 1, 2, 3, and water. The viscosity is the variable parameter in this calculation. Fluid 1 does not show detectable variation from water, while Fluid 2 and Fluid 3 show differences due to the increase in viscosity (100 times for Fluid 2 and 1000 times for Fluid 3).

Figure 20:
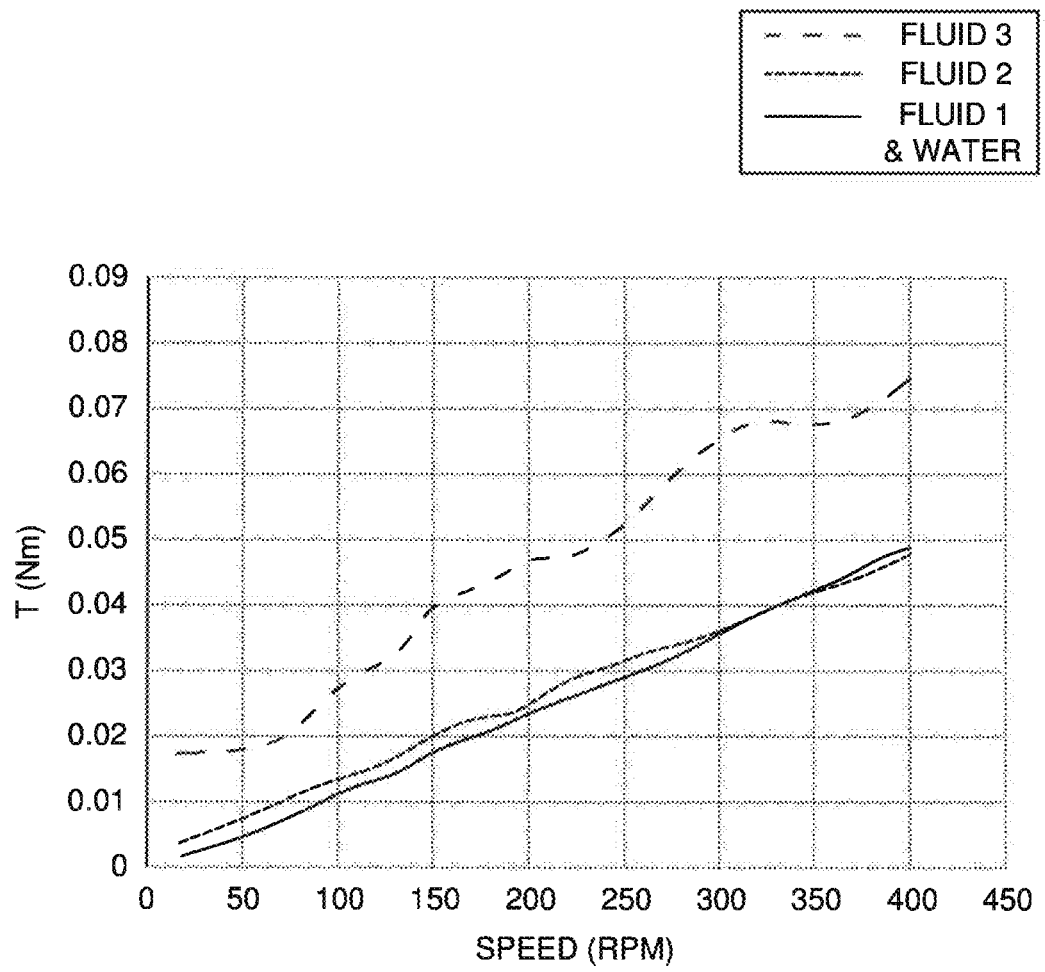
FIG. 20 illustrates the variation in torque-speed slope (dT/dn) for different viscosities, as shown by Fluids 1, 2, 3, and water.

FIG. 20 shows the variation in torque-speed slope for different viscosities. The variation in slope is minimal when varying the viscosity, while the variation in y-axis crossing point is differentiated. Again, Fluids 1, 2, 3, and water are plotted; Fluid 1 does not show detectable variation from water.

Figure 21A:
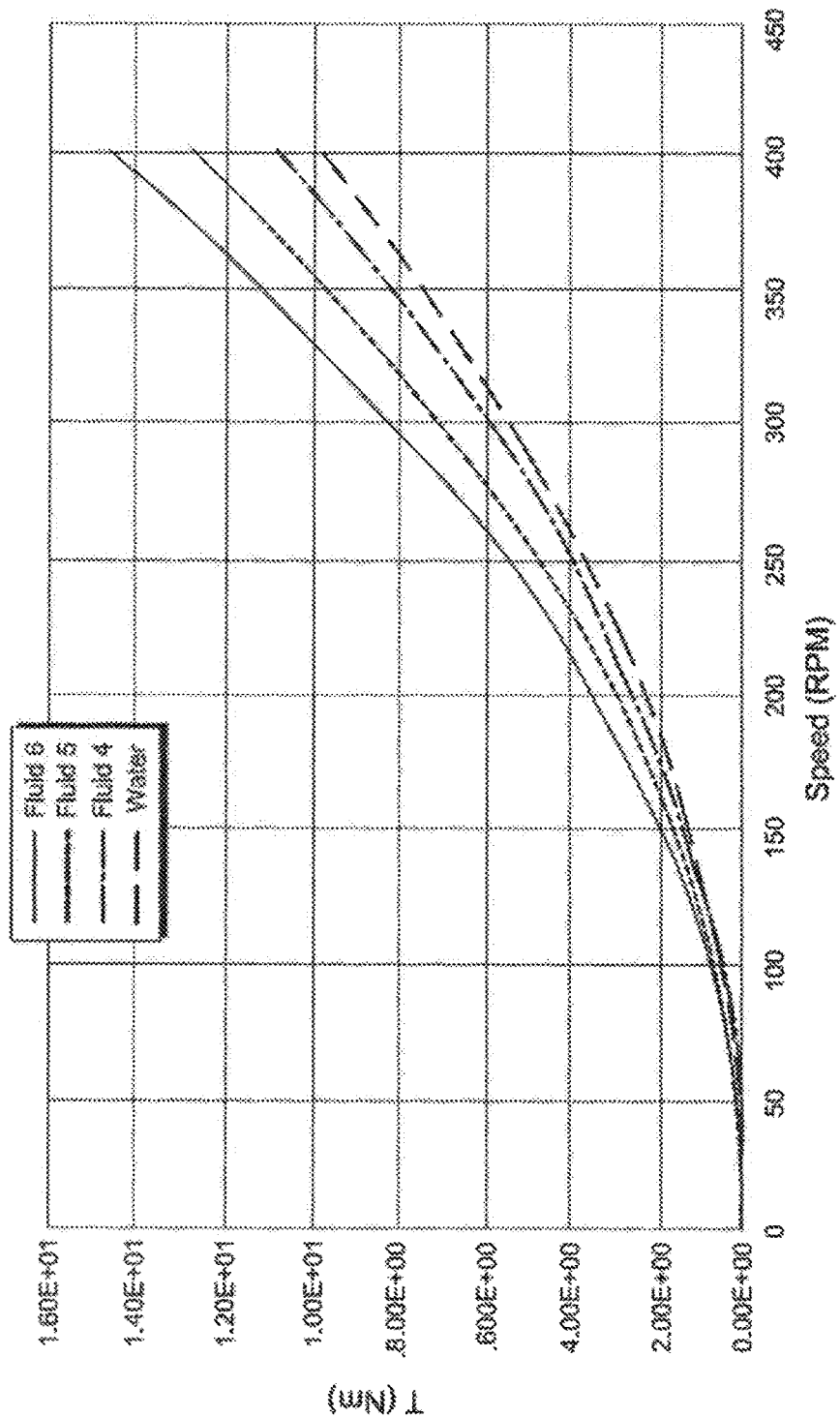
FIG. 21A shows the variation of impeller torque as a function of rotating speed for Fluids 4, 5, 6, and water, whereby the viscosity is kept constant and density is varied to 1.1×, 1.3×, and 1.5×, respectively.

FIG. 21A shows the variation of impeller torque as a function of rotating speed for Fluids 4, 5, and 6 as compared to water. The viscosity is kept constant and density is varied (relative to the density of water) to 1.1×, 1.3×, and 1.5×, respectively. The variation of density is detectable for the fluids.

Figure 21B:
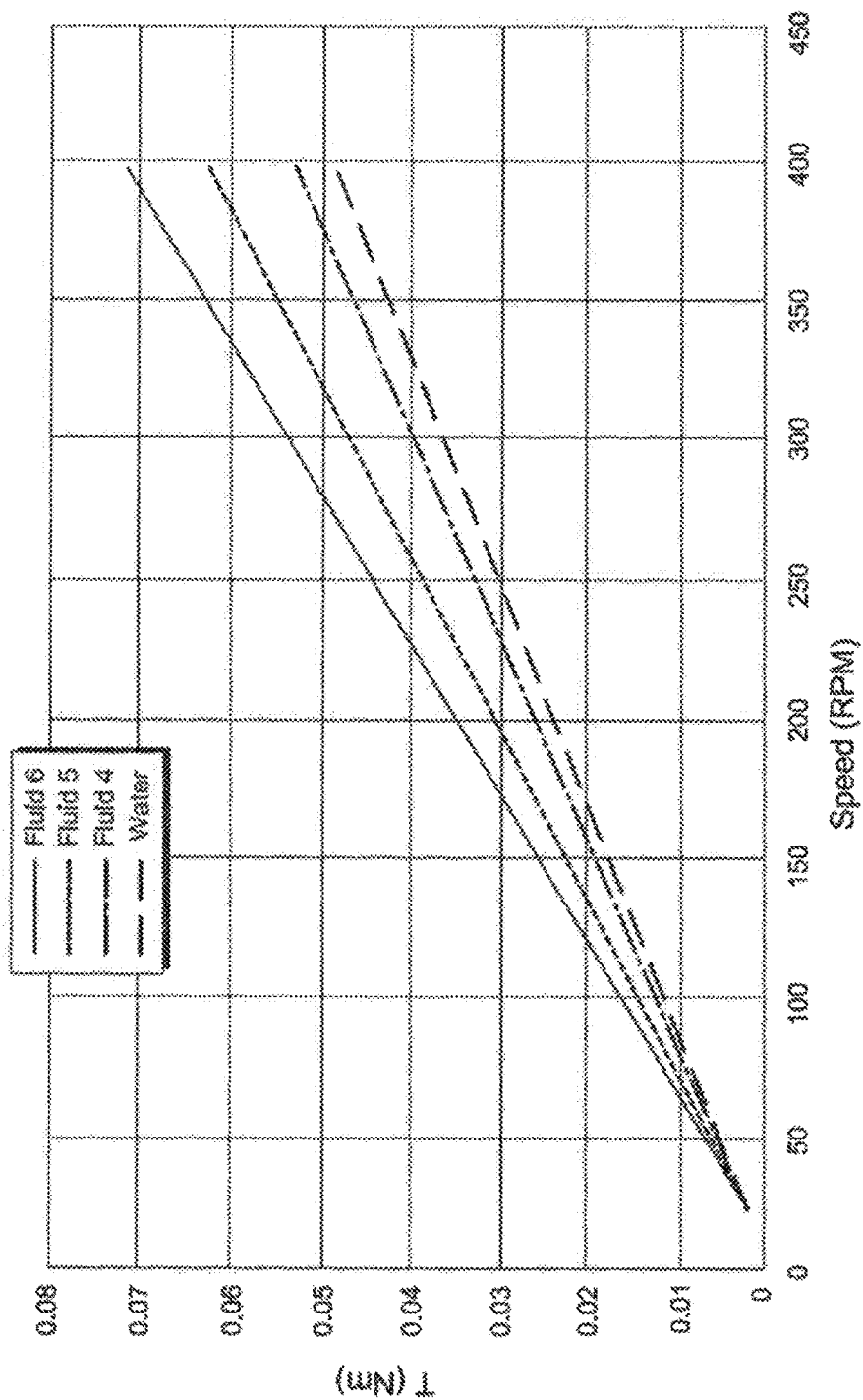
FIG. 21B shows the variation in torque-speed slope for different fluid densities in one embodiment.

FIG. 21B shows the variation in torque-speed slope for different fluid densities of Fluids 4, 5, and 6 as compared to water. While the variation in slope due to viscosity is minimal, the density effects the slope, and minimally, the y-axis intercept.

Hence, following the relationships outlined above, the change of viscosity in a fluid may be detected by measuring the impeller torque at different speeds. In addition, changes in density are detectable at various levels. By studying the torque-speed slope, the variation in fluid properties can be distinguished between variations in viscosity or density.

Embodiments below describe the method of measuring the torque for bioreactors and various types of mixers.

To measure the torque and speed of an impeller, transducers can be installed on the shaft, in the space between the impeller and drive, on the impeller magnets, or on the drive magnet or core as additional components.

Method 1: Measuring Torque and Speed as Related to Magnet-Magnet Coupling

Figure 22A:
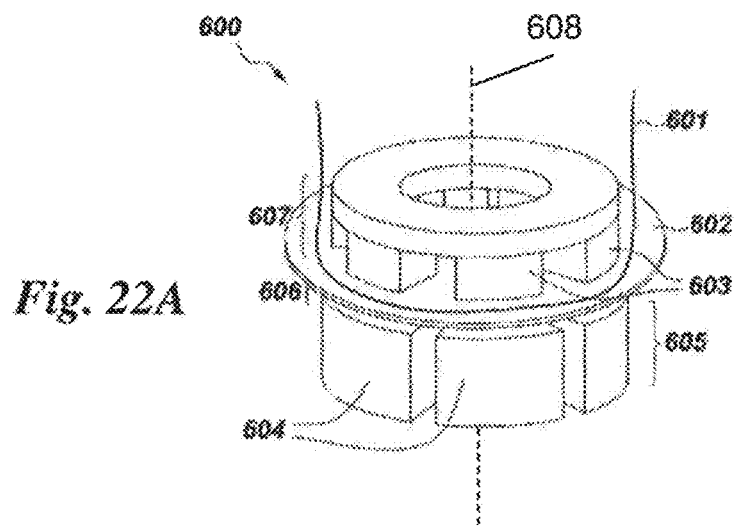
FIG. 22A is a perspective view in one embodiment of a printed circuit board (PCB) winding incorporated between an arrangement of magnets to pick up the back electromotive force (EMF).
Figure 22B:
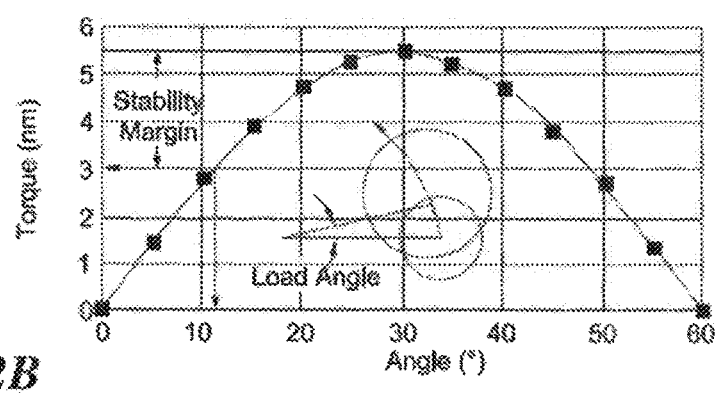
FIG. 22B is a graphical depiction of the torque versus load angle in one embodiment.

Embodiments of the invention include a sensor positioned outside a bag or vessel, outside the closed system, that does not allow for electrical wiring inside the bag. In one aspect, the sensor is integrated with the drive head. FIG. 22A depicts a system 600 with a printed circuit board (PCB) winding 602 incorporated with an arrangement of magnets 603, 604 of an axial flux stator 605. The system 600 includes a first set of magnets 603 at the impeller end 607 (rotatable around central axis 608), the impeller end positioned within a vessel 601, and a second set of magnets 604 positioned at the drive end 605. The PCB winding 602 is a single coil, or set of coils as shown in greater detail of FIG. 22C, and placed between the sets of magnets 603, 604 in the area 606 where the magnetic gradient is arranged. FIG. 22B demonstrates that synchronous torque depends on load angle, such that the angle between the rotor and the stator fluxes (i.e., the angle between the rotor pole (or magnet) and the stator pole (or magnet)). By placing a single coil or a set of coils, such as the printed circuit board (PCB) winding 602, between the stator 605 and the rotor 607, the magnetic flux in the space or area 606 between the drive and the impeller (partially or fully filled with air) can be detected and related to the produced torque. In one aspect, a single coil or the set of coils are printed on a circuit board, and can be arranged and placed in a single layer or multi-layers.

Figure 22C:
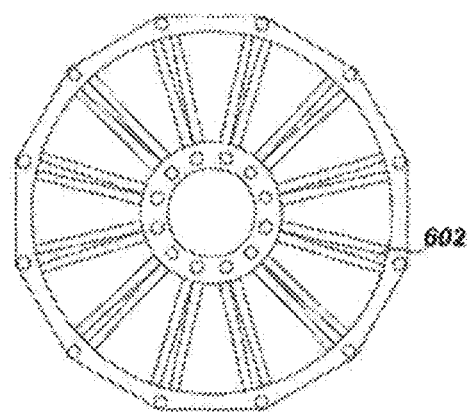
FIG. 22C is an embodiment of a flux sensor, here a printed circuit board (PCB) winding, that is utilized to acquire flux information and estimate torque.

In one embodiment, a flux sensor, such as the PCB winding 602 (shown in FIG. 22C) is installed on an existing magnet-magnet coupling of a bioreactor, or mixer system, to acquire flux information and estimate torque. The flux sensor functions to acquire the speed by relating the measured voltage to the speed of rotation. The voltage, as it changes with time, is measured at various instances. In FIG. 22C, the illustration depicts a PCB winding 602 that picks up the back electro-motive force (EMF).

Figure 24:
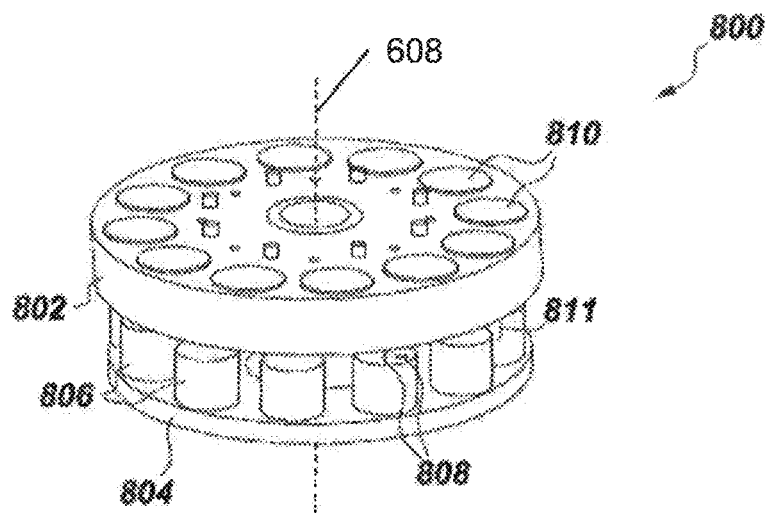
FIG. 24 is an embodiment of bioreactor drive and impeller comprising 12 magnets on each, between which the magnetic flux or the magnetic field density sensor(s) are placed.

In one embodiment, a magnetic field density sensor 808 (e.g., one or more 3D hall-effect based sensors, anisotropic magnetoresistance (AMR), shingled magnetic recording (SMR), giant magnetoresistance (GMR) sensors), and shown in FIG. 24, is installed in the space between the drive and the impeller. The magnetic field density in this space changes as the torque produced by the impeller changes. FIG. 24 depicts a magnet-magnet coupling bioreactor system 800, using integrated sensors 808 to measure the varying viscosity and varying density when the system is in use. Impeller magnets 810 at the impeller end 802 form a first portion and the drive-end magnets 806 incorporate with a base steel plate 804 form a second portion. As depicted, sensors 808, including magnetic field density sensors, are integrated with a drive magnet 806. The sensors, however, may be incorporated, integrated, and/or placed within any region of the system 800. Specifically, the sensors shown are integrated within the region 811 between the impeller-end magnets and the drive-end magnets. The produced torque relates to the fluid properties (e.g., weight, volume, viscosity, density). At speed n dT/dn, T is used to identify fluid viscosity, density, and different operating conditions.

Method 2: Measuring Torque and Speed as Related to Axial Flux (AF) Stator

Figure 23:
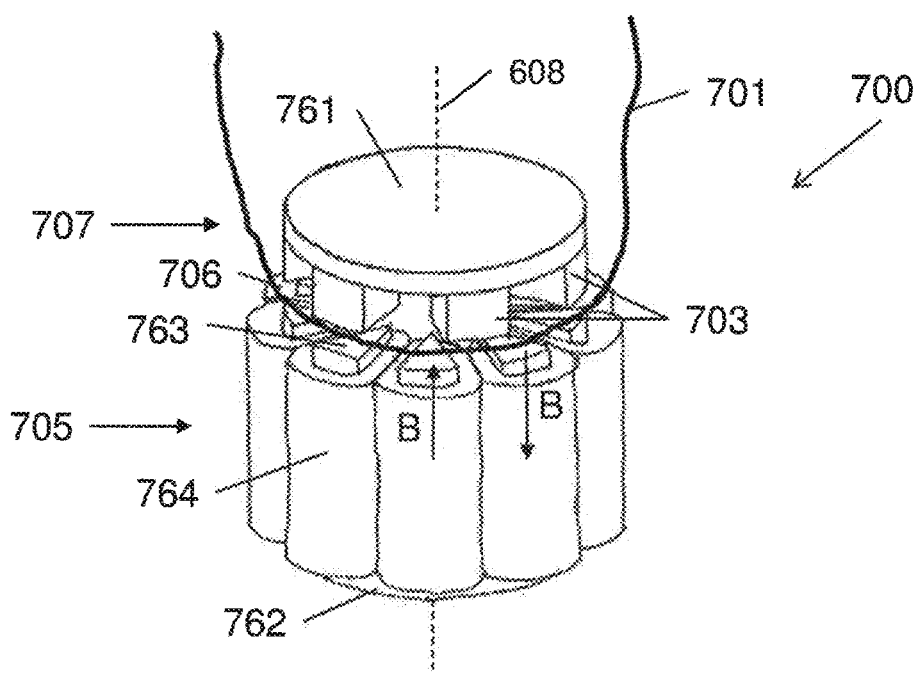
FIG. 23 is a perspective view of an embodiment of an axial flux stator with the magnetic arrangement, and assembled with an impeller portion.

With the axial flux stator, as shown in FIG. 23, the stator voltages and currents are acquired and decomposed to direct and quadrature axis components, and back EMF and torque are calculated without the need for sensors. FIG. 23 illustrates an embodiment of a device 700 having a first rotor portion 707 positioned within a vessel 701, and a second stator portion 705; the second stator portion is a tooth wound axial flux stator 705 that comprises pie-shaped magnetic stator teeth 763 that extend vertically from the stator back iron 762. The stator core can be formed from sintered powdered iron, ferrite, or machined from a coil of magnetic steel. Conductive windings (current carrying elements) 764 are wound around the stator teeth 763. The conductive windings are divided into phases. Within each phase winding, the field direction of the individual coils alternates so that the application of phase current to the phase winding creates a magnetic field (B) that is directed vertically upward in one tooth and vertically downward in another tooth. The flow of current through the conductive windings forms a magnetic field that flows through the stator teeth, across the air gap, or region 706 between the stator 705 and a rotor 761, interacts with the magnets 703 on the rotor, travels through the rotor 761, and returns through a rotor magnet 703 of opposite magnetic polarity, across the air gap between the stator and rotor, through an oppositely-excited stator tooth, closing through the stator back iron 762.

While Method 1 is described in terms of the magnet-magnet coupling system 800 and can be applied to several different arrangements of drive and impeller, Method 2 is specific for wound stator drive system 700 as shown in FIG. 23. The magnet-magnet coupling system leverages the change in magnetic field density and/or magnetic flux to produce information on the position of the impeller and hence, the produced torque and/or speed. The stator drive system acquires the input current and voltage to the wound stator and relates such information to the produced torque and/or speed.

Figure 25A:
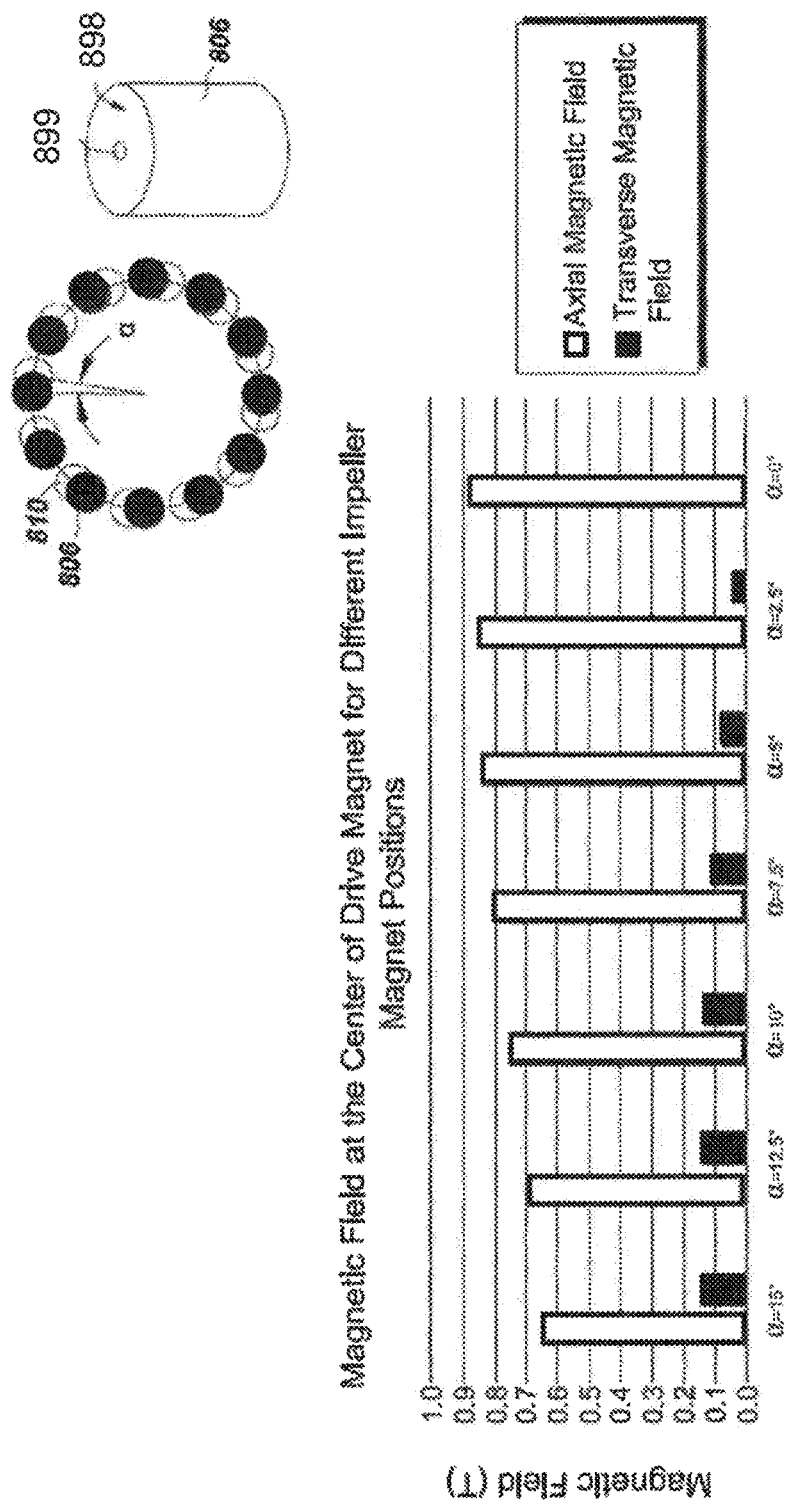
FIG. 25A shows the variation in the axial and the transverse magnetic field densities when measured on the top of the drive magnet, using a magnetic sensor, at different impeller positions.

FIG. 25A shows a comparison of the magnetic field density acquired on the center point 899 of a top surface 898 of one drive magnet 806 (see FIG. 24) for different impeller positions. Impeller positions are recorded as the angle difference between the center line of the impeller magnets 810 and the corresponding center line of the drive magnet 806. The density of the magnetic field is recorded in both axial and transverse directions and it shows significant differences as the impeller-drive angle changes. These values are directly related to the produced torque and are used to deduce the produced torque.

Figure 25B:
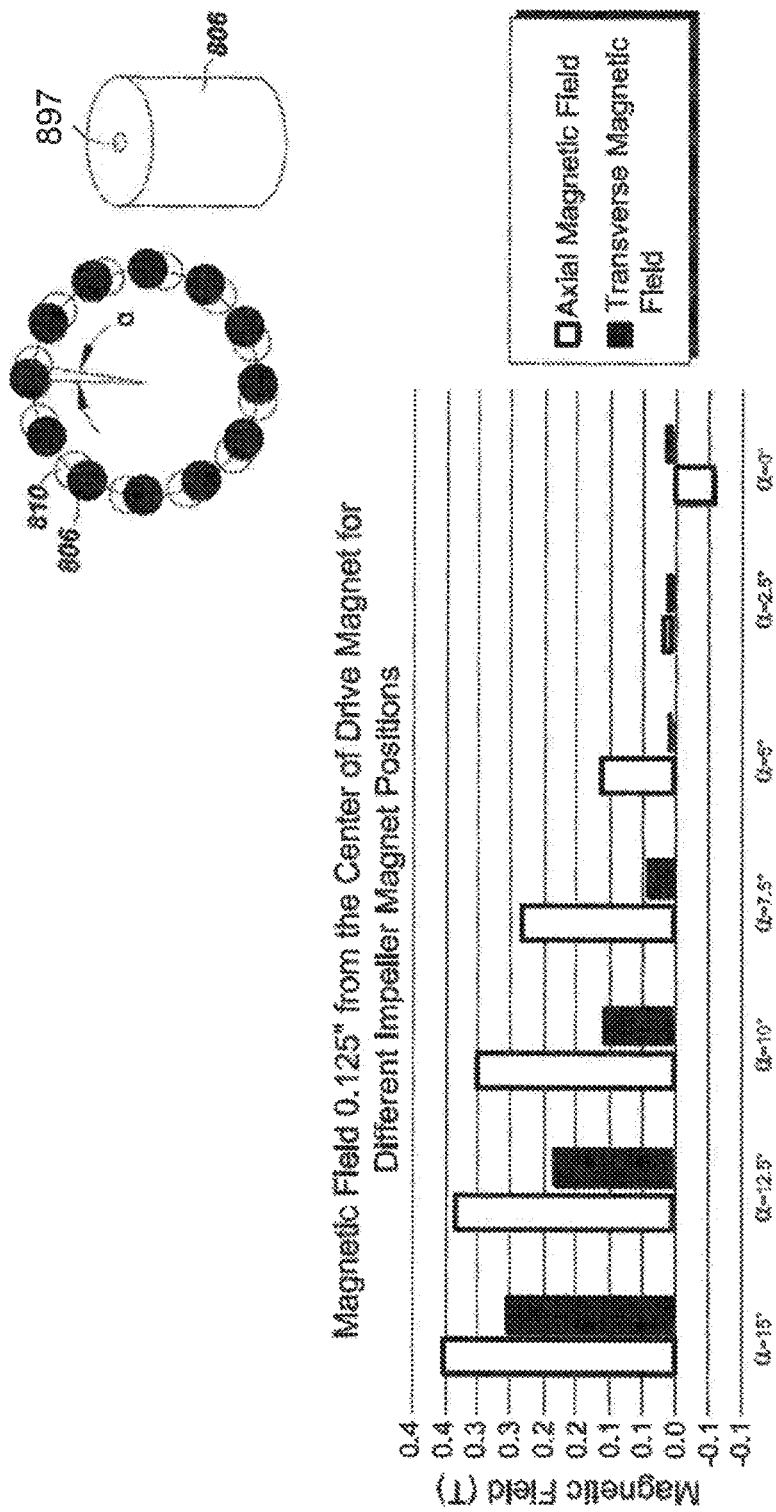
FIG. 25B shows the variation in the axial and the transverse magnetic field densities when measured 0.125" (3.2 mm) from the top of the drive magnet, using a magnetic sensor, at different impeller positions.

FIG. 25B is similar to figure FIG. 25A with the difference of the point of measurement. Here, the point of measurement 897 is shifted ⅛$^{th}$ of an inch (3.2 mm) in the axial direction towards the impeller, the point of calculation is 0.125" (3.2 mm) above the center 899 of the drive magnet 806. Again, the changes in magnetic field density is relative to changes in the impeller magnet 810 position. The sensor position can be anywhere between the drive and the impeller, or even on the bottom surface of the drive or the top surface of the impeller.

Figure 25C:
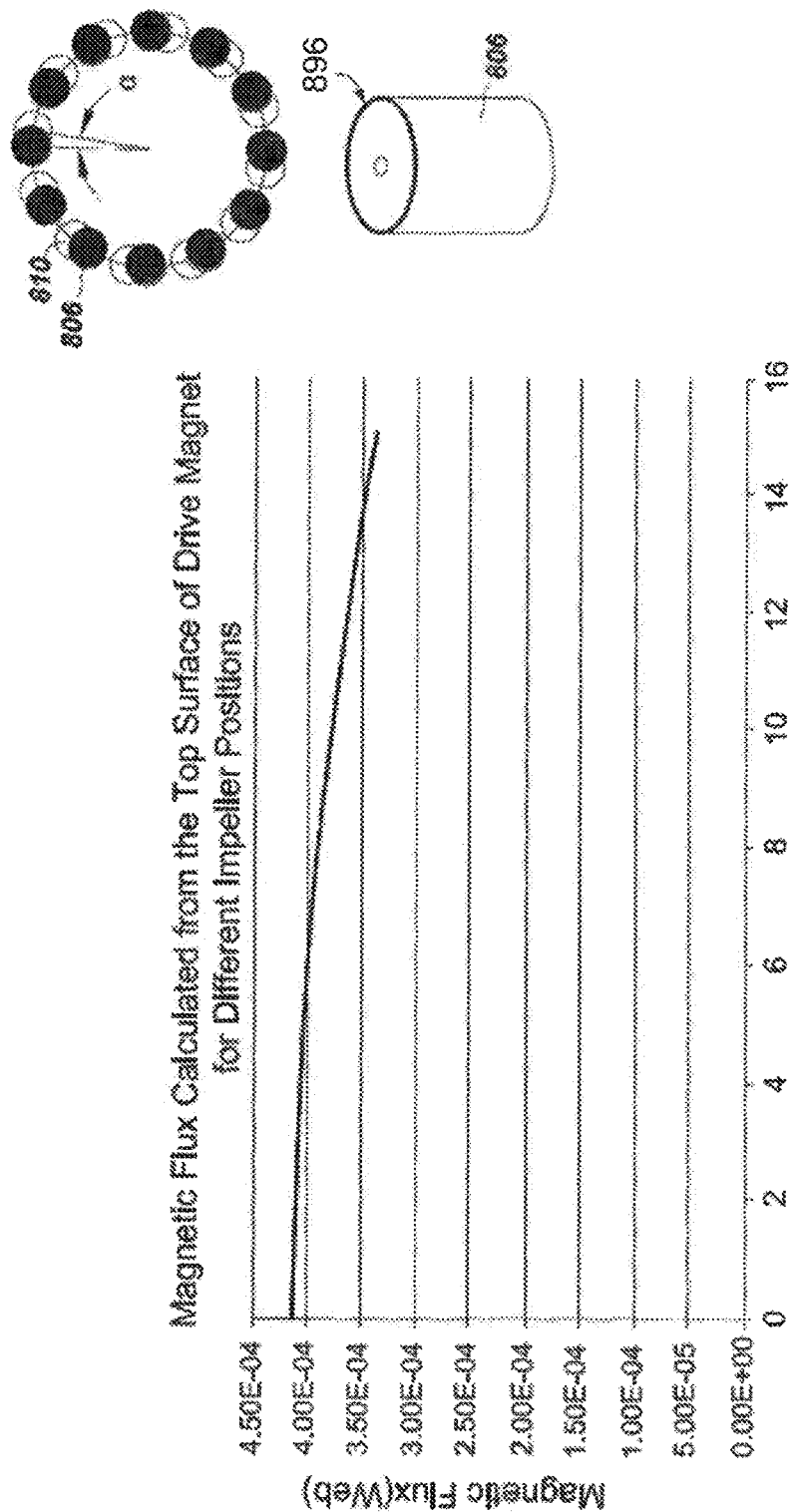
FIG. 25C shows the variation in the magnetic flux when measured by a loop placed on the top circumference of the magnet, using PCB winding or pick-up coil, at different impeller positions.

FIG. 25C shows the change in magnetic flux for different impeller positions. It is clear that the magnetic flux can also be used to detect the impeller position and hence the produced torque. Since the flux changes with impeller relative position, it can be used also to detect sudden impeller position, relative to drive, changes. This can be explained using Faraday's law:

$$e = -N \frac{d\phi}{dt}$$

Here, e is the produced voltage in the loop, used to pick-up the magnetic flux, N is the number of turns of the loop, and ϕ is the magnetic flux through the loop 896. A change in the impeller relative position causes a sudden change in the loop voltage (since the voltage is related to time-change on the magnetic flux) and hence, this change in voltage can be related to the change in the impeller relative position. If the impeller speed increases over a certain time (t), then the voltage during this period can be used to calculate the new impeller relative position and speed. If the impeller changes relative position suddenly, due to an abnormal condition, then the voltage waveform is very short in time (more like a pulse) and hence an abnormality behavior can be detected and a subsequent action triggered.

Figure 26:
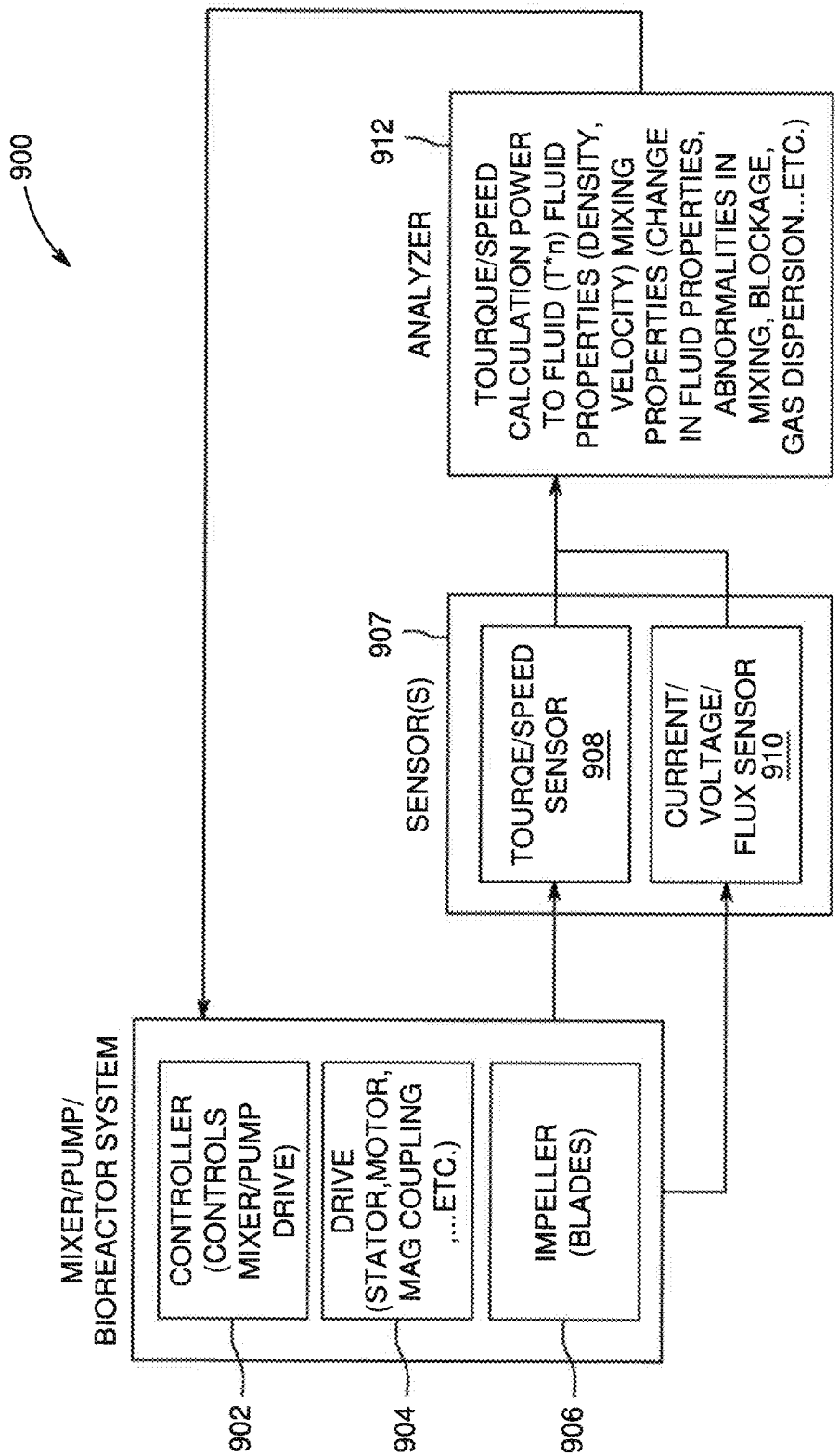
FIG. 26 illustrates an embodiment of the mixing process in a schematic defining the implementation of one or more sensor(s) with the mixing system.

FIG. 26 is a schematic of a mixer system 900. In one aspect, the mixer system is a pump. In another aspect, the mixer system is a bioreactor system. The mixer 900 includes a controller 902; a drive 904 includes a stator, a motor, magnetic coupling, among other components; and an impeller 906 includes one or more blades, among other components. The controller 902 controls the mixer and/or pump drive 904. The drive may include any one of a stator, motor, magnetic coupling, alone or in combination. The sensor arrangement 907 includes a torque-speed sensor 908, a current/voltage/flux sensor 910, alone or in combination. The sensors 907 relay information to a processor 912 which analyzes the torque and speed calculation, analyzes power provided to the fluid, fluid properties (e.g., density, viscosity, etc.), mixing properties (e.g., change in fluid properties, abnormalities in mixing, blockage, gas dispersion, etc.), and other analyses as selected. The processor then provides direction to the controller 902 in a feedback loop. In this manner, the processor is an analyzer that provides precise control of the mixer to increase or decrease agitation, direct power into the system, adjust fluid properties, and correct any deficiencies, abnormalities, or otherwise.

Aspects herein include the assessment of the angle in between the drive and the impeller during mixing operations. This allows for determination of torque, viscosity, and other fluidic properties. This provides a common feature between the dedicated sensor (See FIG. 22C, sensor 602) and the indirect measurement with the axial flux stator.

In one embodiment, the angle in between the drive and the impeller is determined by optical methods such that a marker on the impeller is read by an optical detection system. In such an embodiment, reflecting light from a fiber would allow ease of detection as the impeller is close to the bag bottom and a transparent window can fit with the bag. Other position indicators are possible as well.

In one embodiment, a discrete Hall sensor is utilized. The signal can be processed and compared against the position of the drive, in either a rotating drive or a flux stator. Calibration for a zero torque (offset) case without liquid or other conditions can also be configured. The use of a magnetic field sensor, direct or indirect, can thus be modified and altered in size, shape, and dimension as desired by a user.

Embodiments disclosed herein have several advantages to supersede systems in the field today. Such benefits include detection of fluid viscosity and density, as well as power and torque, delivered to the fluid inside the mixer. Obstructions are detected during start-up, including for example, sediment of micro-carriers, cells or undissolved powder in the bottom of the mixer. Torque measurements enable determination of power transmitted to fluid by actual measurement, in contrast to using solely empirical impeller power number and speed according to Eq. 1), hereby allowing for actual mass transfer determination (e.g., gas transfer calculations). In addition, flooding of the impeller in multiphase systems (e.g., gas sparged bioreactor) can be detected. Changes and any issues in gas sparging can be detected. Correct positioning of the disposable unit, and its impeller, can be verified. Measurement and monitoring of the different properties can also be used for the process analytical tool (PAT).

Embodiments further address the challenges and issues that arise in the field. Determination of power delivered to the fluid is currently performed with formulas or look-up tables and not directly measured. Fluid density and/or viscosity changes as the mixing process takes place, thus, updated values provide accurate control of the mixing process. Abnormalities in mixing process, such as blockage, obstacles, or issues with gas sparging, may also be determined to ensure quality of the mixing process. These features detect and flag such issues, possibly even providing an alarm, so that the mixing process can be corrected.

Embodiments disclosed herein provide additional functionalities to the user of the bioreactor or mixer, as desired. Various embodiments allow accurate monitoring of the power delivered to the fluid while mixing, and allow continuous updates on the fluid properties, including alarms in cases of abnormalities in mixing. Such embodiments may be modified so as to encompass features and components such as temperature, pressure, and other measurable conditions. The embodiments and aspects disclosed herein may be incorporated with any size, shape, and dimension of vessel, bag, mixing container or otherwise.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The invention claimed is:

1. A system utilized as a bioreactor mixer, the system comprising:
   a rotation drive, wherein the rotation drive comprises a stator;
   a shaft;
   an impeller capable of rotating around a central axis;
   a plurality of magnets, the plurality of magnets comprising a first set of magnets in a first array format positioned at a drive end adjacent the rotation drive and a second set of magnets in a second array format positioned at the impeller; and
   one or more magnet sensors configured to detect the magnetic field or a magnetic flux, and positioned with the system to detect the magnetic field or the magnetic flux.

2. The system of claim 1, wherein the second set of magnets forms a Halbach array.

3. The system of claim 1, wherein the shaft is a fixed shaft and the impeller is capable of rotating around the fixed shaft.

4. The system of claim 1, wherein the shaft is fixed to the impeller and capable of rotating with the impeller around the central axis.

5. The system of claim 1, wherein the drive stator is an axial flux stator positioned on an underside of the plurality of magnets.

6. The system of claim 5, wherein the axial flux stator comprises a control circuit to control the voltage and current, individually or in combination, provided to the stator.

7. The system of claim 5, wherein the axial flux stator comprises a control circuit to measure the torque and speed of rotation.

8. The system of claim 5, wherein the axial flux stator comprises a control circuit to measure the magnetic flux and magnetic flux density produced by the axial flux stator and impeller magnets.

9. The system of claim 8, wherein the axial flux stator comprises a plurality of current carrying elements to produce magnetic flux in an axial direction and drive the impeller.

10. The system of claim 9, wherein the axial flux stator comprises a core to fix the plurality of current carrying elements on.

11. The system of claim 10, wherein the core is magnetic or non-magnetic.

12. The system of claim 1, wherein the drive stator is mounted in a wall of a rigid support vessel and the impeller and shaft are located in a flexible bioreactor bag adapted to be received in the rigid support vessel.

13. The system of claim 1, wherein the drive stator is mounted in a bottom wall of a rigid support structure.

14. The system of claim 12, wherein the flexible bioreactor bag comprises an impeller receiver structure adapted to receive the impeller and shaft and to align them with the drive stator.

15. The system of claim 14, wherein the impeller receiver structure comprises a fixed shaft that is adapted to receive the impeller and to align it with the drive stator.

* * * * *